United States Patent
Refai et al.

(10) Patent No.: US 12,357,152 B2
(45) Date of Patent: *Jul. 15, 2025

(54) ARTIFICIAL INTELLIGENCE-BASED MEDICAL 3D SCANNER

(71) Applicant: Optecks, LLC, Bixby, OK (US)

(72) Inventors: Hakki Refai, Bixby, OK (US); Badia Koudsi, Bixby, OK (US)

(73) Assignee: Optecks, LLC, Bixby, OK (US)

( * ) Notice: Subject to any disclaimer, the term of this patent is extended or adjusted under 35 U.S.C. 154(b) by 30 days.

This patent is subject to a terminal disclaimer.

(21) Appl. No.: 18/191,595

(22) Filed: Mar. 28, 2023

(65) Prior Publication Data

US 2023/0380659 A1 Nov. 30, 2023

Related U.S. Application Data

(63) Continuation of application No. 16/201,614, filed on Nov. 27, 2018, now Pat. No. 11,617,492.

(Continued)

(51) Int. Cl.
*A61B 1/00* (2006.01)
*A61B 1/05* (2006.01)
(Continued)

(52) U.S. Cl.
CPC ......... *A61B 1/000094* (2022.02); *A61B 1/00* (2013.01); *A61B 1/00135* (2013.01);
(Continued)

(58) Field of Classification Search
CPC ............... A61B 1/000094; A61B 1/00; A61B 1/00135; A61B 1/00172; A61B 1/00179; A61B 1/00193; A61B 1/00194; A61B 1/051; A61B 1/0676; A61B 5/065; G06T 7/33; G06T 7/521; G06T 7/557; G06T 7/73; G06T 2207/10012; G06T 2207/10028;
(Continued)

(56) References Cited

U.S. PATENT DOCUMENTS

2004/0064018 A1* 4/2004 Dunki-Jacobs ...... A61B 1/0684
600/178
2009/0036902 A1* 2/2009 DiMaio ..................... A61B 8/12
606/130

(Continued)

FOREIGN PATENT DOCUMENTS

WO WO 2016/127173 8/2016

OTHER PUBLICATIONS

International Search Report and Written Opinion regarding PCT Serial No. PCT/US18/62627 mailed Feb. 27, 2019.

*Primary Examiner* — Anne M Kozak
*Assistant Examiner* — Kaitlyn E Sebastian
(74) *Attorney, Agent, or Firm* — DUNLAP CODDING, P.C.

(57) ABSTRACT

Systems and methods for three-dimensional imaging, modeling, mapping, and/or control capabilities in compact size suitable for integration with and/or augmentation of robotic, laparoscopic, and endoscopic surgical systems. The systems including at least one optical source configured to project onto a surgical or endoscopic environment, and at least two cameras positioned to capture at least one image of the surgical or endoscopic environment.

20 Claims, 12 Drawing Sheets

Related U.S. Application Data

(60) Provisional application No. 62/590,956, filed on Nov. 27, 2017, provisional application No. 62/608,433, filed on Dec. 20, 2017, provisional application No. 62/669,072, filed on May 9, 2018.

(51) Int. Cl.
| | |
|---|---|
| *A61B 1/06* | (2006.01) |
| *A61B 5/06* | (2006.01) |
| *G06T 7/33* | (2017.01) |
| *G06T 7/521* | (2017.01) |
| *G06T 7/557* | (2017.01) |
| *G06T 7/73* | (2017.01) |
| *H04N 13/239* | (2018.01) |
| *H04N 13/254* | (2018.01) |
| *H04N 23/55* | (2023.01) |
| *H04N 23/957* | (2023.01) |
| *H04N 13/20* | (2018.01) |
| *H04N 23/11* | (2023.01) |
| *H04N 23/50* | (2023.01) |

(52) U.S. Cl.
CPC ...... *A61B 1/00172* (2013.01); *A61B 1/00179* (2013.01); *A61B 1/00193* (2013.01); *A61B 1/00194* (2022.02); *A61B 1/051* (2013.01); *A61B 1/0676* (2013.01); *A61B 5/065* (2013.01); *G06T 7/33* (2017.01); *G06T 7/521* (2017.01); *G06T 7/557* (2017.01); *G06T 7/73* (2017.01); *H04N 13/239* (2018.05); *H04N 13/254* (2018.05); *H04N 23/55* (2023.01); *H04N 23/957* (2023.01); *G06T 2207/10012* (2013.01); *G06T 2207/10028* (2013.01); *G06T 2207/10048* (2013.01); *G06T 2207/10052* (2013.01); *H04N 13/20* (2018.05); *H04N 23/11* (2023.01); *H04N 23/555* (2023.01)

(58) Field of Classification Search
CPC .......... G06T 2207/10048; G06T 2207/10052; H04N 13/239; H04N 13/254; H04N 23/55; H04N 23/957; H04N 13/20; H04N 23/11; H04N 23/555; H04N 13/25; H04N 13/271

See application file for complete search history.

(56) References Cited

U.S. PATENT DOCUMENTS

| | | | |
|---|---|---|---|
| 2010/0249506 | A1* | 9/2010 | Prisco ................. A61B 1/0051 600/117 |
| 2014/0268041 | A1 | 9/2014 | Copland |
| 2016/0242761 | A1* | 8/2016 | Lore .................. A61B 17/0469 |
| 2018/0270474 | A1* | 9/2018 | Liu ........................... G06T 7/30 |

* cited by examiner

ARTIFICIAL INTELLIGENCE-BASED MEDICAL 3D SCANNER

CROSS-REFERENCE TO RELATED APPLICATIONS

This present application is a continuation application of and claims priority to U.S. patent application Ser. No. 16/201,614, filed on Nov. 27, 2018, titled "Medical Three-Dimensional (3D) Scanning and Mapping System", which claims the benefit of U.S. Ser. No. 62/590,956, filed on Nov. 27, 2017; U.S. Ser. No. 62/608,433, filed on Dec. 20, 2017; and U.S. Ser. No. 62/669,072, filed on May 9, 2018; which are all hereby incorporated by reference in their entirety.

BACKGROUND

Currently, surgeons perform over 7.5 million laparoscopic procedures worldwide, with over 3.5 million laparoscopic procedures performed in the U.S. alone last year. The introduction of new, innovative devices expected to make laparoscopic procedures more efficient and improve clinical results will lead to an expected increase to 4 million laparoscopic procedures in the U.S. by 2021. Despite the expected growth, laparoscopic and robotic assistive surgical techniques remain constrained by the limited availability and range of tools, unlike open surgical procedures where surgeons have access to a very wide range of tools for almost any situation during surgery. Even with such limitations, the advantages of laparoscopic surgery, the advances in robotic surgery introduced by Intuitive Surgical in the daVinci system, and the planned introduction of new robotic surgical systems from other manufacturers, continue to expand use of such systems, with, for example, over 4,271 daVinci systems deployed and in use worldwide.

Colonoscopy provides a key instrument for detecting and preventing colorectal cancer, the second leading cancer-related cause of death in the U.S., with nearly 1 in 3 patients dying from the condition. When performed correctly, colonoscopies can find precancerous polyps and adenomas, facilitate removal or treatment of polyps and adenomas, and provide early detection of colorectal cancer. A lack of professionals trained in the procedure, combined with a miss rate of up to 20.7% and 22.9% for polyps and adenomas, respectively, by trained professionals, places limits on the number of patients that undergo the procedure and the efficacy of the procedures. As the population ages, the need for colonoscopy procedures will continue to grow, despite the fact that the number of personnel trained to perform the procedure will not grow sufficiently fast to meet the increased demand.

The prior art uses visible light systems that provide images of the surgical space or the patient's colon but lack capabilities that would enhance the performance of minimally-invasive surgical procedures and colonoscopy procedures. First, the visible light systems lack the ability to make accurate intra-operative measurements. Until recently, the most common measurement methods consisted of inserting a flexible ruler through the surgical sleeves, measuring the surgical instrument prior to surgery, and subjective measuring based on the surgeon's prior experience. For hernia repair surgery, failure to accurately measure the size and shape of the hernia can lead to improper sizing and shaping of the patches [1,2], not placing suture for closing the hernia within 3-6 mm of the fascial edges [4-7], and errors in preparing pockets for inserting the patch. Second, current visible light systems only see forward, which can cause the physician to miss details along the sides of the tool unless the physician turns the instrument to look sideways. For example, during a colonoscopy the physician may miss small polyps and adenomas with coloring that blends in with the coloring of the colon tissue or that lie behind folds in the colon tissue, preventing treatment of polyps until the polyps threaten the patient's health.

Current visible light systems cannot provide three dimensional data, mapping, and modeling of the procedural space, limiting monitoring of the environment during surgical or colonoscopy procedures, the ability to provide data to the physician that may help guide the surgical tools or endoscope, and the ability to compile a patient record for monitoring health over time. For example, during abdominal surgeries, the surgeon must avoid damage to vital organs and blood vessels that would cause harm to the patient. During colonoscopy, optimal operation requires driving the endoscope at or close to the center of the colon and full cecal intubation all within an optimal time window. Additionally, the visible light system cannot provide sufficient data about the surgical space to support development of autonomous and semi-autonomous systems to perform difficult tasks such as suturing and guiding endoscopes, through tight curved spaces like the throat, brachial tubes, and the colon. The visible light system also cannot produce detailed, three-dimensional modeling, mapping, and imaging of the procedural space that would support augmented reality-based displays to guide surgeons or colonoscopy operators and support the development of simulators for surgical and colonoscopy procedures.

U.S. surgeons perform approximately 350,000 to 500,000 ventral hernia repairs and 600,000 inguinal hernia repairs annually, with about 30% using minimally invasive methods [9-10]. The CDC estimates that colonoscopies prevented 66,000 colorectal cancers and saved 32,000 lives between 2003 and 2007.

In many surgical procedures, including hernia repairs, surgeons need to make exact incisions or cuts to ensure a successful surgical procedure. Examples include, but are not limited to, making a cut of a specific length to insert a medical device or to access a surgical site safely, and cutting a specific distance away from the edge of a tumor or diseased area of tissue to ensure removal of the unwanted tissue while minimizing trauma to surrounding healthy tissue. For non-invasive surgeries, surgeons cannot utilize measurement tools available for use in open surgical procedures, and current non-invasive systems provide limited, if any, tools for making measurements during procedures. Only through extensive training and experience can surgeons develop and refine the ability to accurately estimate distance within the surgical space given only the image provided by the visible light system. Many medical facilities use CT scans to measure the herniated area to allow selection of patch size prior to surgery. The mesh area to defect area (M/D) ratio provides the only independent predictive factor for hernia recurrence [1], with a recurrence rate of 70%, 35%, 9% and 0% for an M/D≤8, between 9 and 12, between 13 and 16, and ≥17, respectively. Despite the pre-operative CT scan, surgeons often must perform intra-operative measurements to improve the probability of success. For example, if the hernia has an irregular shape, the surgeon needs accurate measurement of the shape, circumference, and total area to ensure sufficient patch overlap. The surgeon must accurately measure intra-operatively pockets prepared for the mesh patch to ensure proper overlap. Precise measurement of defects and prepared pockets prove crucial for obtaining the best possible outcomes, as 8.5% of hernia recurrence cases result from selecting a patch size too small to cover the hernia adequately [11]. Closing the hernia requires the surgeon to place stitches within 3-6 mm of the fascial edge [4-7], a precision that requires real-time, millimeter-accurate imagery. Avoiding damage or trauma to critical organs and large blood vessels requires a system that provides real time proximity measurements.

In colonoscopy, several factors contribute to the rate of missed polyps and adenomas, including the insertion and withdrawal time, cecal intubation rate, quality of bowel preparation, the size, shape, and number of polyps, and the quality of the imaging system, particularly for detecting adenomas. In addition, the availability of an assistant in some form to augment the capabilities of the physician performing the colonoscopy increases the efficacy of the procedure, even when the performing physician does not possess training in the procedure, such as a primary care physician. The assistant could consist of a physical person present during the procedure, a person on-call to provide support during difficult parts of the procedure, or augmenting existing visible light imagery with data, text, directional icons, and highlighting based on real-time, high-accuracy mapping of the colon tissue around the endoscope. A system that combines high-accuracy scanning hardware and sophisticated mapping software would provide the level of assistance needed to elevate the success rate of colonoscopies, especially the success rate of colonoscopies performed by untrained personnel, thereby improving access to effective colonoscopy procedures at a level that meets both current and future demand.

In early 2018, Intuitive Surgical introduced a mechanical intra-operative measurement feature for the DaVinci robotic surgical system after many years of development. In the system, a surgeon clicks a button, physically moves the surgical head, and then clicks the same button. Software utilizes inputs from the surgical head to measure the distance moved. To measure in multiple directions, the operator must perform multiple passes. The measurement system cannot transition to use in colonoscopy procedures.

Auris Surgical Robotics recently introduced the Monarch Platform, a flexible robotic endoscopic system that received FDA approval for bronchoscopic procedures. For measurement, the Auris system constructs a three-dimensional map from a collection of two-dimensional pre-operative CT scans. The operator drives the endoscope during the procedure using the three-dimensional map as a guide [14-23]. However, the three-dimensional map lacks the accuracy to detect polyps and adenomas, especially those smaller than 6 mm in size, which makes the process unsuitable for use in colonoscopy procedures. Sensors provide additional feedback on the endoscope's position and orientation.

Advantis Medical Systems recently unveiled its Third Eye Panoramic System in an attempt to improve detection of polyps and adenomas located behind folds in the colon wall. The Advantis system consists of a module containing two side facing, wide angle source-camera pairs mounted on the side of the endoscope. The additional imaging systems provide imagery of the walls around the endoscope head to the operator and illumination that can penetrate a larger fraction of folds. The system design presents a significant difficulty to the operator. The system displays three separate images on the screen, one for each camera, requiring the operator to simultaneously monitor and process three images to detect polyps instead of a single, integrated view of the colon.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION

Figure 1A:
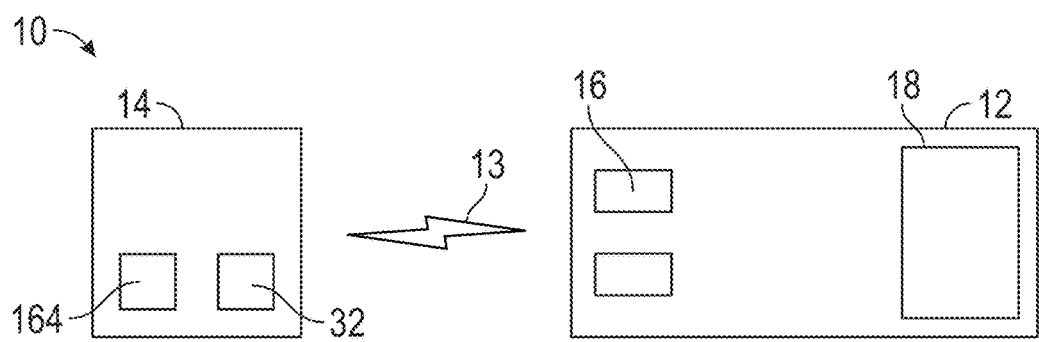
FIG. 1A is a block diagram of an exemplary medical scanning and mapping system of the present disclosure.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The disclosure is capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

Referring now to the Figures, and in particular to FIG. 1A, shown therein and designated by reference numeral 10 is an exemplary medical scanning and mapping system 10 in accordance with the present disclosure. Generally, the medical scanning and mapping system 10 may be used as a stand-alone system or a system integrated into currently used and future envisioned medical systems (e.g., endoscopic systems currently used). In some embodiments, the medical scanning and mapping system 10 may be used in minimally invasive surgical procedures such as endoscopic surgery, robotic surgery, and/or the like. In some embodiments, the medical scanning and mapping system 10 may be used in endoscopic procedures, including, but not limited to lower endoscopy procedures (e.g., colonoscopy) and/or upper endoscopy procedures. Using the system and methods described herein, the medical scanning and mapping system 10 may adapt to and/or augment current surgical and endoscopic procedures and/or currently available systems for which other methods for performing medical imaging cannot provide a solution.

The medical scanning and mapping system 10 described herein may provide three-dimensional imaging, modeling, mapping, and control capabilities in compact size suitable for rapid (e.g., immediate) integration with and/or augmentation of robotic, laparoscopic, and endoscopic surgical systems. Generally, the medical scanning and mapping system 10 may include one or more optical hardware systems 12 configured to scan and capture one or more high resolution images of a three dimensional environment during minimally-invasive surgery and endoscopic procedures, for example. Additionally, the medical scanning and mapping system 10 may include an image reconstruction system 14 configured to process the one or more images to provide data to a surgical and/or endoscopic operator.

Data may include, but is not limited to, one or more dynamic three dimensional measurements of one or more features (e.g., polyp(s) in the colon or hernia dimension(s)), one or more three-dimensional reconstructions of a surgical or endoscopic environment for analysis, patient baseline medical data, augmented reality displays configured for guiding a surgeon and/or operator through each part of a procedure, one or more warnings of surgical or endoscopic instruments endangering surrounding tissues and organs. Data may be analyzed and/or used to supply one or more control signals configured to enable development of autonomous and semi-autonomous robotic surgical and endoscopic systems for performing procedures.

Generally, the one or more optical hardware systems 12 may illuminate a surgical or endoscopic environment with one or more specifically designed light source(s) 16, and capture one or more images of the illuminated environment with one or more specialized, high-resolution cameras 18. Described herein are four exemplary configurations for the optical hardware system 12: a plenoptic camera coupled to standard light source, a single or two high-resolution cameras coupled to a structured or patterned light source, modulated light source with time-of-flight camera, and specialized camera-source combinations. However, it should be noted that additional configurations including combinations thereof are contemplated.

FIG. 1A illustrates an exemplary embodiment of the optical hardware system 12. The optical hardware system 12 may include, but is not limited to, one or more optical sources 16, and a camera 18. The one or more optical sources 16 may be configured to emit light at wavelengths suited for the particular surgical or endoscopic environment such that surrounding tissue may be illuminated. In some embodiments, the one or more optical sources 16 may consist of uniform optical intensity emitted in all directions. In some embodiments, the one or more optical sources 16 may be configured to emit at an intensity capable of decreasing with increasing angle (e.g., fiber optic light sources).

The one or more optical sources 16 may be configured to deliver significant optical power to a tissue without causing damage to the target tissue and/or a patient due to heating and/or other interactions with high optical intensities. The one or more optical sources 16 may include a laser or light emitting diode (LED) operating in the visible region of the optical spectrum, for example. In some embodiments, the operating region is in the visible range between 390 nm and 700 nm. The one or more optical sources 16 may provide sufficient power for reflection from the tissue to be captured with sufficient contrast by the high resolution camera 18 (e.g., plenoptic, light field camera, high resolution camera), but low enough power to avoid damage to the patient and/or to saturate sensors of the high resolution camera 18. In some embodiments, the one or more optical sources 16 may produce illumination that lacks structure, including but not limited to, uniform illumination intensity over space and deterministic spatial changes such as the Gaussian distribution of power with angular direction from the optical axis of the source common with LEDs or the output of optical fiber.

In some embodiments, optical power from the one or more optical sources 16 may be delivered to the position of surgical or endoscopic evaluation via an optical fiber, fused array of fibers or similar waveguide positioned through and/or about a tubular sleeve or endoscopic tool. One end of the optical fiber may be formed as a flat surface or curved surface (e.g., spherical or parabolic shape). In some embodiments, optical power from the one or more optical sources 16 may be delivered to the position of surgical or endoscopic evaluation via an extended source located at or near an end of a tubular sleeve or endoscopic tool, powered through an electrical cable positioned (e.g., strung) from an external power supply through the tool to the optical source 16. Possible sources include, but are not limited to, any visible LED with a broad emitting area, including an organic LED (OLED), that emit in the preferred wavelength range. Any such source may include mechanisms for mitigating heat emitted from the source if needed. Other methods for delivering the optical power from the optical source 16 to the point of surgery or endoscopic evaluation are contemplated.

The image reconstruction system 14 may be configured to process the images to retrieve three dimensional details of the environment and construct one or more three dimensional models of the environment. For example, the image reconstruction system 14 may provide image reconstruction in the form of three-dimensional or two-dimensional modeling of target tissue and/or environment. The image reconstruction systems 14 are able to embody and/or execute the logic of the processes described herein. Logic embodied in the form of software instructions and/or firmware may be executed on dedicated system or systems, on distributed processing computer systems, and/or the like. In some embodiments, the logic may be implemented in a stand-alone environment operating on a single system and/or logic may be implemented in a networked environment such as a distributed system using multiple computers and/or processors. For example, microprocessors of the image reconstruction system(s) 14 may work together or independently to execute processor executable code using one or more memories 32. To that end, in some embodiments, the image reconstruction system 14 may be integral to the optical hardware system 12 and/or communicate via one or more networks 13. For example, in some embodiments, a single processor may be positioned external to the optical hardware system 12 and communicate via a wired or wireless network 13 such that the processor may be external to a patient body during use. In some embodiments, multiple processors of the image reconstruction system 14 may be positioned internal and/or external to the patient body during use. For example, at least one processor of the image reconstruction system 14 may be positioned with the optical hardware system 12 and communicate with an external processor of the image reconstruction system 14 during use.

Figure 1B:
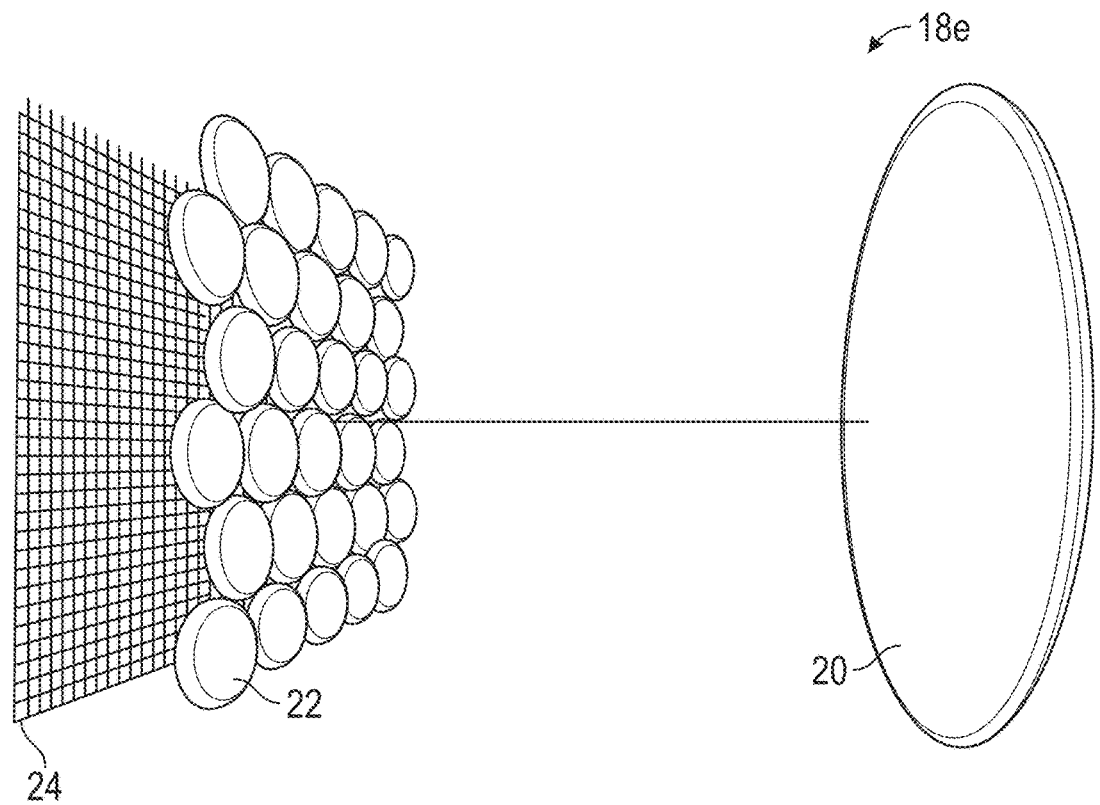
FIG. 1B is a block diagram of an exemplary camera for use in the medical scanning and mapping system illustrated in FIG. 1.

FIG. 1B illustrates an exemplary embodiment of a camera 18e for use in the medical scanning and mapping system 10. In this embodiment, the high-resolution camera 18e may be a plenoptic camera or light field camera. The plenoptic or light field camera 18e is an optical recording device capable of capturing both the variation of intensity with spatial position and the angle or direction of rays entering the system from each part of the scene observed by the camera 18e. The plenoptic or light field camera 18e may include, but is not limited to, an imaging lens system 20 that may be configured to create a local image of the scene contained within the lens system's field of view; a microlens array 22 placed after the imaging lens system 20 at a specific location with respect to the focal length of the imaging lens system 20; and a light detecting array 24 placed at a distance after the microlens array 22. The microlens array 22 may cause displacement of parts of the image that are not in focus after imaging through the imaging lens system 20. Effectively each pixel on the light detecting array 24 may view the image from a different angle or perspective. The displacement provides information to the specialized processing software needed to extract depth information about the scene contained within the lens system's field of view.

The image reconstruction system 14 may include one or more processors having analysis software configured to convert image data recovered from the light detecting array 24, perform calculations to extract depth information, and construct one or more three dimensional models of the scene of interest. Images recovered from adjacent lenses in the microlens array 22 may show the same point in space from slightly different positions. The software uses information about the power and period of the microlens array 22, the position of the microlens array 22 with respect to the imaging lens system 20 and the light detecting array 24, and the period and size of the pixels within the light detecting array 24 to perform calculations that determine the three-dimensional position of each point within the scene. The software uses the three-dimensional position information from all of the points to construct one or more three-dimensional depth maps of the entire image. The software combines the three-dimensional depth map with raw two-dimensional image data from the light detecting array 24 to construct a three-dimensional mapping or view of the scene. Software for forming the three-dimensional mapping or view of the scene can be obtained from vendors that include, but are not limited to, Raytrix, having a principle place of business in Kiel, Germany, and Lytro, having a principle place of business in Mountain View, California.

Figure 2:
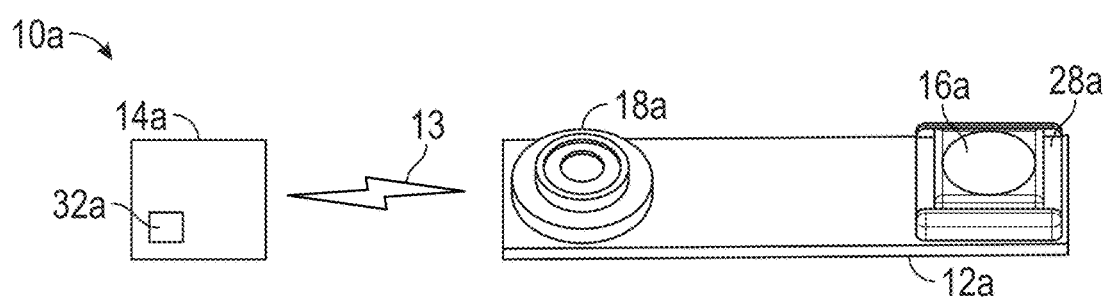
FIG. 2 is a block diagram of another exemplary medical scanning and mapping system of the present disclosure.
Figure 3:
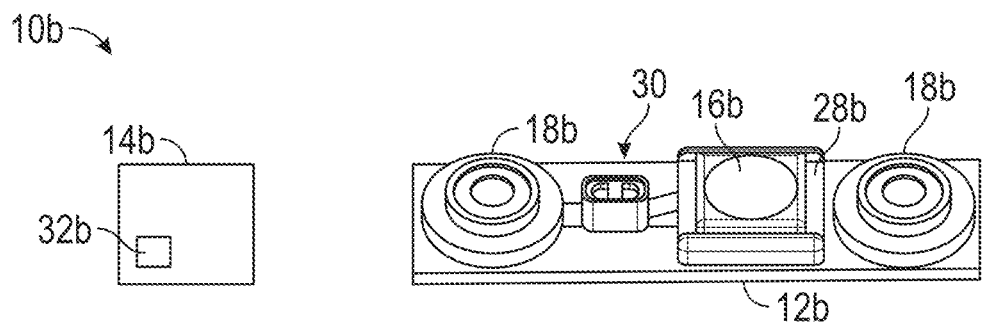
FIG. 3 is a block diagram of another exemplary medical scanning and mapping system of the present disclosure.

FIGS. 2 and 3 illustrate exemplary embodiments of medical scanning and mapping systems 10a and 10b having one or two high-resolution cameras 18a and 18b, and optical hardware systems 12a and 12b, respectively. The optical hardware systems 12a and 12b may include a pattern generator 28 as described in further detail herein.

Generally, the medical scanning and mapping system 10a in FIG. 2 may include an optical hardware system 12a having an optical source 16a configured to provide infrared light to illuminate tissue and a single high-resolution camera 18a. Additionally, the optical hardware system 12a may include an optically-based pattern generator 28 configured to impose structured light consisting of light with regular and controlled spatial variations in intensity, referred to as spatial patterns. The spatial patterns may consist of, but are not limited to, arrays of dots, lines, and other geometric figures, and may or may not also contain color variations.

The single high resolution camera 18a may be sensitive to infrared light, and possibly both infrared and visible light. The single high resolution camera 18a may be configured to capture one or more images of tissue(s) within the surgical or endoscopic environment illuminated by the optical source 16a.

The properties of the optical hardware system 12a and single high resolution camera 18a, including each of the optical source(s) 16a and pattern generator 28a, the arrangement with respect to each other and the configuration of the complete optical hardware system 12a within the tubular sleeve or endoscopic tool determine performance of the medical scanning and mapping system 10a in terms of lateral resolution, the depth of tissue for which the target resolution is achieved, and the field of view over which the medical scanning and mapping system 10a can make measurements.

The image reconstruction system 14a may perform one or more matching operations, wherein each part of a projected pattern is subsequently matched to a component of the original pattern stored in the software memory 32a (associate components of the pattern recorded in the camera image with the corresponding point in the original projected pattern). In this way, the software determines which part of the original pattern illuminated each section of tissue within the surgical or endoscopic environment. The image reconstruction system 14a may use the matching information, along with information about the geometrical arrangement of the camera and source, as input to sophisticated triangulation algorithms. The triangulation algorithms use the information to calculate a location in 3D space for each segment of the surgical or endoscopic environment. Repeating the process for two different patterns projected on the same section of tissue may increase the accuracy of the triangulation process and allows the system to produce highly accurate 3D spatial reconstructions of the illuminated environment.

FIG. 3 illustrates another exemplary embodiment of a medical scanning and mapping system 10b having an optical hardware system 12b with a structured light source. The optical hardware system 12b may include two high-resolution cameras 18b, an optical source 16b and pattern generator 28b. The optical source 16b may be similar to the optical source 16a described herein.

The two high-resolution cameras 18b may be located at two different positions with respect to the optical source 16b. Each high-resolution camera 18b may be configured to capture an image (e.g., simultaneously or intermittently) of the illuminated surgical or endoscopic environment.

The properties of the optical hardware system 12b and two high resolution cameras 18b (including each of the optical source(s) 16b and pattern generator 28b), the arrangement with respect to each other and the configuration of the complete optical hardware system 12b within the tubular sleeve or endoscopic tool determine performance of the medical scanning and mapping system 10b in terms of lateral resolution, the depth of tissue for which the target resolution is achieved, and the field of view over which the medical scanning and mapping system 10b can make measurements.

The image reconstruction system 14b may perform a matching operation in which software attempts to determine where the same component of the projected pattern appears within both of the captured images from each of the cameras 18b, using the original pattern stored in the software's memory 32b. The software uses the location of each pattern component in the two images from the two high resolution cameras 18b and information on the geometry between the two cameras 18b as input to the sophisticated triangulation algorithms. The triangulation algorithms use the information to calculate a location in 3D space for each segment of the surgical or endoscopic environment, and subsequently constructs a highly accurate 3D spatial model of the illuminated environment.

The medical scanning and mapping system 10b illustrated in FIG. 3 utilizes the two high resolution cameras 18b to record the pattern projected by the pattern generator 28b onto the surrounding tissue. Utilizing two cameras 18b provides stereoscopic viewing of the projected pattern, allowing recovery of depth information independent of the position of the optical source 16b with respect to the two cameras 18b. As a result, the number of potential locations of the optical source 16b on the optical hardware system 12b increases. Possible source locations may include, but are not limited to, any location along the line between the cameras 18b, to the left or right side of both cameras 18b, and a distance along the direction perpendicular to the line between the cameras 18b. The optical source 16b illuminates the tissue within the field of view of the cameras 18b regardless of the position of the optical source 16b in order to construct a model of the targeted tissue.

The optical sources 16a and 16b of the systems 10a and 10b in FIGS. 2 and 3 may deliver significant optical power to the tissue under investigation without causing damage to the target tissue. Additionally, the optical sources 16a and 16b may reflect sufficient power from the target tissue to be captured with sufficient contrast by the cameras 18a and 18b. The optical sources 16a and 16b may include a laser or light emitting diode (LED) operating in the visible or infrared region of the optical spectrum. In some embodiments, the operating region may be in the near infrared (NIR) range between 700 nm and 1000 nm. Wavelengths may include 780 nm, 808 nm, 850 nm, or 980 nm, as these wavelengths are available in commercial sources, provide maximum optical reflection from biological tissue, and are sufficiently far from the visible light region of the optical spectrum to avoid interfering with the visible light camera used for robotic surgical and endoscopic procedures. Methods for delivering the optical power to the point of surgery include, but are not limited to optical power from the optical source 16b delivered to the point of measurement via an optical fiber, fused array of fibers or similar waveguide strung through the tubular sleeve or endoscopic tool and terminating at the end of the tube. The end of the fiber may be formed as a flat surface or as a curved surface and may include one or more lenses to spread the light. A curved surface could include, but is not limited to, having a spherical or parabolic shape. In some embodiments, the optical power may be delivered via an extended source located at or near the end of the tubular sleeve or endoscopic tool, powered through electrical cable strung from an external power supply through the sleeve or endoscopic tool to the optical source 16b. Possible sources include, but are not limited to, any infrared LED with a broad emitting area, including an organic LED (OLED), that emit in the preferred wavelength range.

The pattern generators 28a and 28b of the systems 10a and 10b of FIGS. 2 and 3 may include an optical element that imposes some form of spatial intensity modulation on the light from the optical sources 16a and 16b respectively. Methods for implementing the pattern generators 28a and 28b include, but are not limited to, one or more diffractive elements. The diffractive elements may utilize micro-scale variations in optical properties to generate specific patterns. The diffractive elements may include, but are not limited to, (a) surface height variations, such as etched gratings and (b) variations in refractive index within a material, such as holographic elements. The elements may be placed directly in front of the optical sources 16a or 16b within or at the end of the tubular sleeve or endoscopic tool, on or within a window existing between the source and the environment external to the sleeve or endoscopic tool, or directly on the optical source 16a or 16b, or the output window of the optical source 16a or 16b itself. Diffractive elements may provide higher power throughput compared to other methods, which may permit the use of a lower power source.

Methods for implementing the pattern generators 28a and 28b also include, but are not limited to, elements with spatially dependent absorption or transmission. These elements may block or prevent some of the optical source 16a or 16b, respectively, from illuminating the tissue and let other areas of the source light through to illuminate the tissue. Possible embodiments include, but are not limited to, patterning of absorptive materials on a surface between the optical source output and the external wall of the tubular sleeve or endoscopic tool, coatings with spatially varying transmission applied to surfaces between the optical source output and the external wall of the tubular sleeve or endoscopic tool, and a mask. The mask may include, but is not limited to, a printed pattern on an otherwise optically transparent surface, with the pattern including areas of high or full transparency, areas of low or zero transparency, and/or areas with transparency between the maximum and minimum.

In each method, the pattern generator 28a and 28b may be located any of a number of possible positions with respect to the optical source 16a and 16b, respectively, and the outer wall of the tubular sleeve or endoscopic tool. Possible placements include, but are not limited to (a) directly upon the output surface of the optical source, such as the output window of an LED or the polished end of a power delivering fiber, (b) a separate optical surface or surfaces located in the distance between the output surface of the optical source and the outer wall of the tubular sleeve or endoscopic tool, or (c) a window transparent to infrared light placed within the outer wall of the tubular sleeve or endoscopic tool. The pattern generator 28a and 28b may impose one of several possible patterns onto the beam's intensity profile. Possible patterns include, but are not limited to, (a) a Cartesian grid of lines, (b) a set of parallel lines in the vertical or horizontal direction or some combination thereof, (c) and a point cloud, including a pattern of bright dots projected onto the surface of the tissue under investigation.

The high-resolution cameras 18a and 18b may be miniature cameras based on the utilized implementation, configured to capture the optical intensity pattern projected onto the tissue under investigation, and convert the captured image or images into data for input into the image reconstruction system. The camera(s) 18a and 18b may be implemented as, but are not limited to, charged coupled device (CCD), complementary metal-oxide-semiconductor (CMOS) or a similar technology that provides sensitivity to the preferred wavelengths of the source. The cameras 18a and 18b may possess sensitivity only for infrared wavelengths or may possess sensitivity at both red-blue-green (RGB) wavelength and infrared wavelengths.

In some embodiments, a band pass or low pass filter, which pass specific wavelengths while blocking others, may be placed in front of or included as part of the cameras 18a and 18b to block optical power in specific parts of the spectrum to minimize noise or to allow different cameras to provide different information to the image reconstruction system. The cameras 18a and 18b may have sufficient resolution in the recording surface to provide the image reconstruction system with a number and density of samples of the captured image sufficient to meet the measurement needs of the intended application. Camera resolution may depend on the size, density, and number of pixel elements contained with the light sensitive area of the cameras 18a and 18b. The cameras 18a and 18b may also have sufficient sensitivity to accurately record light patterns projected onto the tissue. Reflectivity of tissue is between 50-60%, depending on the type of tissue under investigation, and thus the optical path between optical source 16a and 16b and camera 18a and 18b, respectively, may incur losses in power.

The cameras 18a and 18b may possess a field of view suitable to the implementation method and the application. In some embodiments, field of views may be in the range of 60°-180°. The cameras 18a and 18b may incorporate a lens or other optical element or combination of optical elements that allows the cameras 18a and 18b to receive light from a specific range of angles, thereby achieving a specific field of view. In some embodiments, the cameras 18a and 18b may include "fish-eye" optics (the integrated optics and recording device collectively referred to as a "fish-eye" camera), that allow the cameras 18a and 18b to record images over a much wider field of view than achievable with other optical systems.

In some embodiments, the optical hardware systems 12a and 12b may employ autofocus optics located after the pattern generator 28a and 28b, at the optical source 16a and 16b and in front of the input optics of the camera 18a and 18b, respectively. The autofocus optics may allow the pattern generator 28a and 28b to adjust the distance at which the pattern appears with highest contrast and smallest features and to ensure the best quality image captured by the camera 18a and 18b. In some embodiments, the autofocus optics may produce the best quality projected pattern at a distance equal to the distance between the pattern generator 28a and 28b and the tissue under investigation. The method for determining the distance to the tissue may include, but is not limited to, a proximity sensor 30 utilizing sound or reflected light integrated with the other components of the patterned light-based pattern generator 28a and 28b. The sensor or other method provides distance information to the autofocus optics for the purpose of adjusting the focal length used by the pattern generator 28a and 28b. The triangulation algorithm also requires the distance information and information on the focal length used by the infrared imaging system to maximize the performance of the image reconstruction system.

The image reconstruction systems 14a and 14b may provide image reconstruction. The number of camera-optical source pairs and relative positioning between the cameras 18a and 18b and optical source 16a and 16b within each camera-source pair determine the depth resolution and field of view (FOV) attained by the measurement system.

Figure 4A:
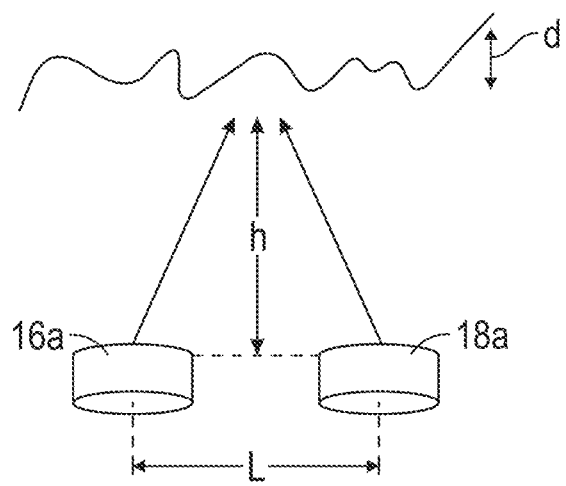
FIG. 4A is a graphical representation of the relationship between lateral distance L between an optical source and camera of a medical scanning and mapping system, distance to an object h of interest, focal length f, and depth d over which high resolution measurements occur.

For depth resolution, the key parameters include the lateral (or baseline) distance between center of the optical source 16a and 16b and the center of the recording area of the camera 18a and 18b, the distance to the object, and the focal length of the imaging optics. Referring to FIG. 4A, the relationship between the lateral distance L, the distance to the object h, the focal length f (in units of pixels on the camera detector array) and the depth d over which high resolution measurements occur is determined by the following equation:

$$d = \frac{h^2}{Lf} c_e \quad \text{(EQ. 1)}$$

wherein d, L, and h are measured in millimeters and $c_e$ is a calibration and matching error correction factor (in pixels) obtained from the calibration process discussed in a later section. The focal length f in pixel units is determined by the following equation:

$$f \text{ (pixels)} = f \text{ (mm)} \cdot \frac{\text{image width (pixels)}}{\text{sensor width (mm)}} \quad \text{(EQ. 2)}$$

The optimum parameter choices depend in part on the system field of view (FOV) and the optical format of the camera 18a and 18b. As one example, if the FOV=60°, the minimum distance to the tissue is 5 cm and the optical format of the camera 18a is ⅔", the lateral (baseline) distance required is 0.5 cm and the required focal length is 7.62 mm. As another example, if the FOV=90° for the same minimum distance and optical format, the lateral (baseline) distance is 0.8 cm and the required focal length is 4.40 mm.

The geometrical configuration of the camera-source pairs determines the FOV and also determines the size and shape of the physical system 10a and 10b and whether the system 10a and 10b is integrated with visible light systems or contained within a separate tubular sleeve used solely for the purpose of making measurements. Examples of how the application and choice of geometry impact the choice of parameters for the scanning system are described herein. For simplicity in description, the medical scanning and mapping system 10a of FIG. 2 will be described in relation to the examples below; however, the examples may also apply to the medical scanning and mapping system 10b of FIG. 3.

In one example, for an endoscopic tool, the medical scanning and mapping system 10a may mount either at the front or along the side of the tubular sleeve, and will typically scan tissue located 4 cm or further from the end or side of the tubular sleeve. For this application, the minimum depth—defined as the depth or distance at which the error in the depth measurement is minimized—is set to 4 cm. The sensor (camera) resolution may be 1280×720 pixels (HD), and the camera FOV may be 90° to scan a large section of the tissue under investigation. For this set of parameters, the distance between the center of the camera 18a and the center of the optical source 16a, called the baseline distance, must be 0.8 cm to achieve a 0.1 mm depth measurement error at the minimum depth. This baseline distance translates into a distance of 1 cm between the outer edge of the camera 18a and the outer edge of the optical source 16a, which keeps the medical scanning and mapping system 10a small enough to fit within the diameter of the front face of the tubular sleeve. This set of parameters achieves a depth error of less than 0.5 mm out to a depth of 10 cm, providing sufficient resolution to meet the application requirements beyond the range of distances expected during the surgical procedure.

If the scanner design uses a camera with a FOV of 60°, the baseline distance needed to achieve the same performance as the cameras with 90° FOV reduces to 0.5 cm. Although the medical scanning and mapping system 10a now scans a smaller tissue area during each recording, the smaller baseline distance allows the scanner to take up less space on the surgical head, and also allows for the integration of multiple scanner elements onto the front or side of the tubular sleeve. Note that the minimum depth for a scanner system using 60° FOV cameras increases to 7 cm if the baseline distance increases to 0.8 cm, and the depth error increases as well to 0.2 mm.

In another example, for procedures such as hernia repair surgery, the medical scanning and mapping system 10a may occupy a platform independent of the tubular sleeves used to perform the surgery. The platform sits on tissue within the surgical space, and thus the maximum dimensions of the platform becomes less restricted by the dimensions of the tubular sleeve and more determined by the dimensions expected in the surgical space. In the example of hernia repair surgery or similar surgical procedures performed in the abdomen, the tissue under repair would typically lie around 10 cm away from the placement of the scanning platform. Assuming the same sensor (camera) parameters used for the endoscopy example and a 90° FOV, the scanning system requires a baseline distance of 2.0 cm (20 mm) to achieve a depth measurement error of 0.2 mm at a minimum depth of 10 cm. A platform with a length of 2.2 to 2.5 cm would fit well within the large abdominal space without impeding the surgical procedure.

Given the relatively large size of the abdominal cavity compared to the colon or esophagus investigated during endoscopic procedures, the optical hardware systems 12a and 12b may utilize cameras with larger FOV to record data from larger areas of tissue. If the camera FOV increases from 90° to 110°, the baseline distance increases to 2.8 cm to achieve a minimum depth of 10 cm and a depth measurement error of 0.2 mm. A scanning platform of 3 cm in length would still minimally impede the surgical procedure and pose minimal risk of potential harm to the patient during the procedure.

Figure 4B:
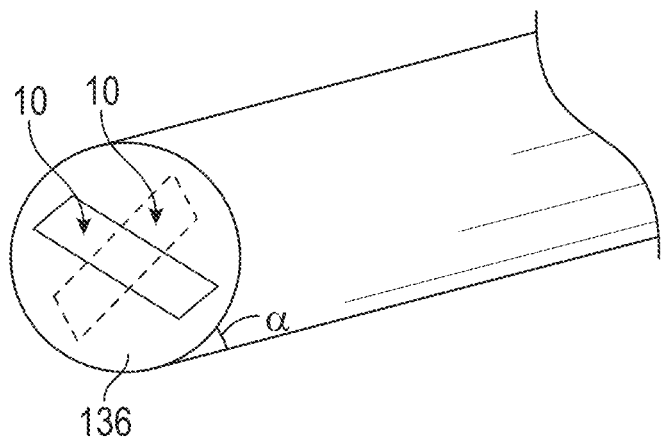
FIG. 4B illustrates a block diagram of an exemplary medical instrument having an angled end face with one or more medical scanning and mapping system positioned at the angled end face.

In another example, if the camera 18a uses an HD format (1920×1080 pixels) and has a 45° FOV horizontally, a diagonal FOV of 50.8°, a sensor width of 3 mm and a sensor height of 1.7 mm, the baseline distance can equal 8 mm between the center of the camera 18a and the center of the projector (optical source 16a or pattern generator 28). For a typical distance of 1.5 mm from center to the edge for both camera 18a and projector, the total system width equals 11 mm, which fits within a 12 mm diameter tube used in laparoscopic systems. Another option includes angling an end face 136 of an instrument to increase the area as illustrated in FIG. 4B. Angling the end face 136 at α=30° relative to a longitudinal axis of the instrument would increase the vertical length of the end face of an 6 mm tube by a factor of two, allowing integration of an 11 mm scanning system 10a. Also, angling the end face 136 at α=45° would increase the vertical length of the end face 136 of an 9 mm tube by a factor of 1.414, allowing integration of an 11.2 mm wide optical scanning system 10a. The theoretical measurement error in depth remains sub-millimeter for depths to 30 cm. Meeting operating objectives of the optical three-dimensional medical scanning and mapping system 10a requires the right balance between the system parameters In another example, if the camera 18a uses an HD format (1920×1080 pixels) and has a 100° FOV horizontally, a diagonal FOV of 107.6°, a sensor width of 5.11 mm and a sensor height of 2.87 mm, the baseline distance can equal 6 mm between the center of the camera 18a and the center of the projector. For a typical distance of 2.6 mm from center to the edge for both camera 18a and projector, the total system width equals 11.2 mm, which fits within a 12 mm diameter tube used in laparoscopic systems. Another option includes angling the end face of the instrument to increase the area. Angling the end face at $\alpha=30°$ relative to the longitudinal axis of the instrument would increase the vertical length of the end face of a 6 mm tube by a factor of two, allowing integration of an 11.2 mm medical scanning and mapping system 10a.

Also, angling the end face at $\alpha=45°$ may increase the vertical length of the end face of a 9 mm tube by a factor of 1.414, allowing integration of an 11.2 mm medical scanning and mapping system 10a. The theoretical measurement error in depth remains sub-millimeter for depths to 5 cm. Meeting operating objectives of the optical three dimensional medical scanning and mapping system requires the right balance between the system parameters.

In another example, if the camera uses an HD format (1920×1080 pixels) and has a 75° FOV horizontally, a diagonal FOV of 82.7°, a sensor width of 2.5 mm and a sensor height of 1.4 mm, the baseline distance can equal 9 mm between the center of the camera 18a and the center of the projector. For a typical distance of 1.4 mm from center to the edge for both camera 18a and projector, the total system width equals 11.5 mm, which fits within a 12 mm diameter tube used in laparoscopic systems. Another option includes angling the end face of the instrument relative to the longitudinal axis of the instrument to increase the area. Angling the end face at $\alpha=30°$ would increase the vertical length of the end face of a 6 mm tube by a factor of two, allowing integration of an 11.5 mm medical scanning and mapping system 10a.

Also, angling the end face at $\alpha=45°$ may increase the vertical length of the end face of a 9 mm tube by a factor of 1.414, allowing integration of an 11.5 mm scanning system. The theoretical measurement error in depth remains sub-millimeter for depths to 9 cm. Meeting operating objectives of the optical three dimensional medical scanning and mapping system 10a may require the right balance between the system parameters.

As described herein, the image reconstruction systems 14a and 14b may provide image reconstruction in the form of three-dimensional or two-dimensional modeling of target tissue and/or environment. The image reconstruction systems 14a and 14b are able to embody and/or execute the logic of the processes described herein. Logic embodied in the form of software instructions and/or firmware may be executed on any appropriate hardware. For example, logic embodied in the form of software instructions and/or firmware may be executed on dedicated system or systems, on distributed processing computer systems, and/or the like. In some embodiments, the logic may be implemented in a stand-alone environment operating on a single system and/or logic may be implemented in a networked environment such as a distributed system using multiple computers and/or processors (e.g., internal and/or external to a patient's body during use). For example, microprocessors of the image reconstruction system(s) 14a may work together or independently to execute processor executable code using one or more memories 32a.

Figure 5:
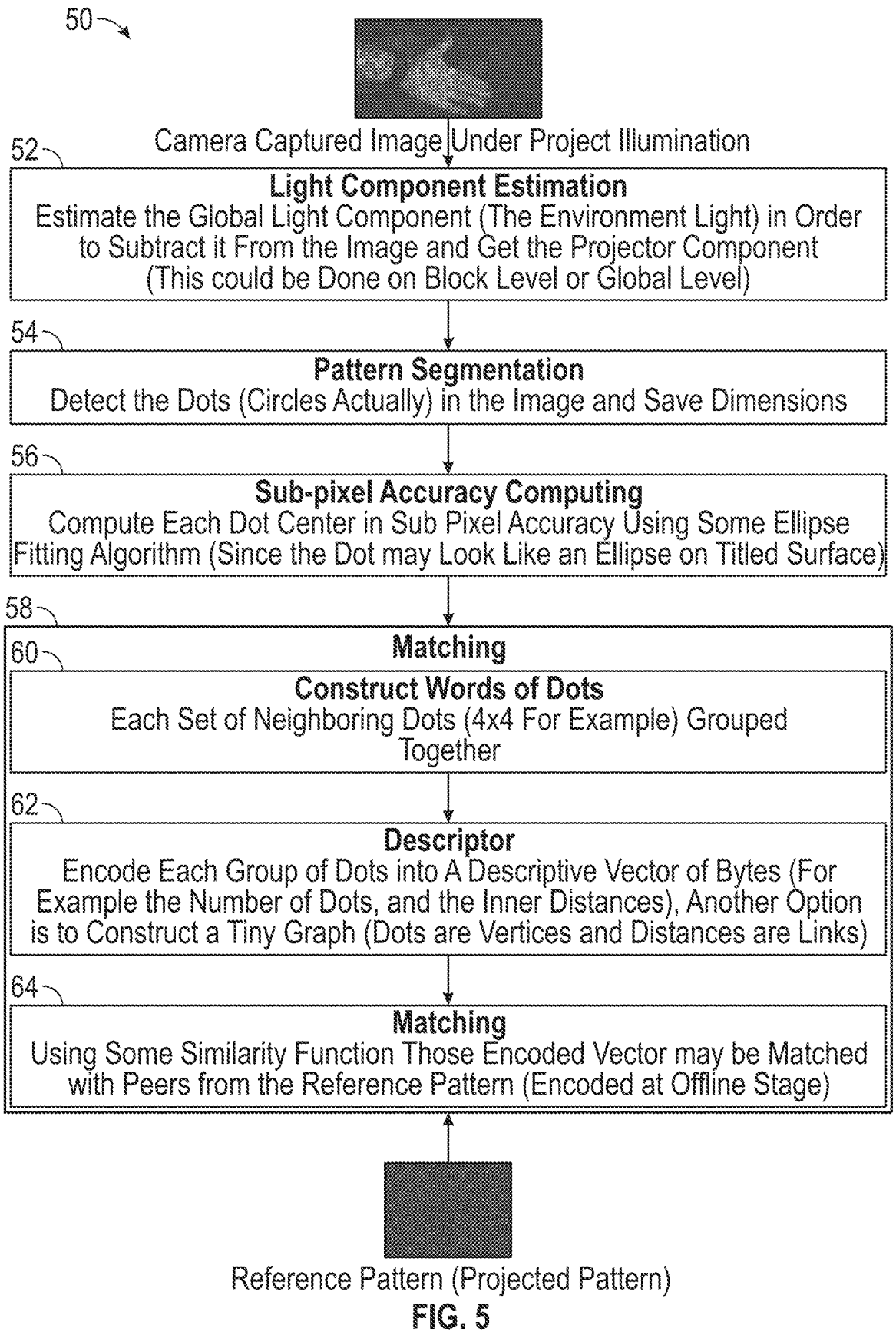
FIG. 5 is a flow chart illustrating a series of operations and calculations performed by an image reconstruction system to produce three-dimensional model(s) and/or measurement data in accordance with the present disclosure.

FIG. 5 is a flow chart 50 illustrating a series of operations and calculations performed by the image reconstruction system 14a to produce three-dimensional model(s) and/or measurement data.

In a step 52, the system 14a performs a light component estimation. After the camera 18a captures an image of the projected light on the tissue, the system 14a produces an estimate of the global light component, also referred to as the environmental or background light intensity. The system 14a subtracts this background component from the captured image to (a) improve the contrast of the projected pattern reflected from the tissue under investigation and (b) capture only the projected pattern illuminating the object for further processing in later stages. The estimation and elimination of the global light component can be performed on either a global level (one estimate for the entire captured image) or on a local level, with the light component estimation carried out in a series of segments or blocks within the image.

In a step 54, the system 14a performs pattern segmentation. The software of the system 14a aims to detect the pattern used at the transmitter to illuminate the tissue under investigation. Knowledge of the pattern helps the software determine which parts of the captured image are adjacent or connected in later stages of processing. For example, a pattern may include a particular arrangement of small dots or circles, and the pattern segmentation stage detects the dots and saves information on the dimension of each dot in the pattern.

In a step 56, the system 14a performs sub-pixel accuracy computing. In particular, the software of the system 14a utilizes approximation algorithms to determine the position of pattern components to within sub-pixel accuracy on the recording surface of the camera 18a. For example, the location of the center of each dot of a pattern would be computed to a sub-pixel accuracy with the assistance of an ellipse fitting algorithm, as projected dots will distort into an elliptical shape when projected onto tilted surfaces of the tissue under investigation.

In a step 58, the system 14a performs pattern matching. At this stage, the image reconstruction system matches elements of the pattern detected by the camera 18a to a reference image, in preparation for performing triangulation. Generally, pattern matching includes three steps. In a step 60, sets of neighboring dots may be grouped together into "words" of the captured pattern. For example, a "word" may include a 4-by-4 configuration of dots (4 dots roughly along the vertical direction and 4 dots roughly along the horizontal direction). Other groups can include, but are not limited to, all of the dots in a subsection of the image (for example, dividing the image into a grid of squares, with each square comprising a subsection of the image).

In a step 62, the system 14a encodes each group or "word" of dots into a descriptive vector of byte. Examples of descriptors include, but are not limited to, the number of dots within the group or "word" and the inner distances (the distances between dots). Another option is to construct a tiny graph, where the dots are vertices linked by lines drawn between the dots, and characterize or encode each group by the properties of the resulting geometric figure.

In a step 64, the system 14a performs matching utilizing one of several available similarity functions that determine how closely a recorded group matches available peer groups contained with the reference pattern. The reference pattern is the original, undistorted pattern delivered to or generated by the optical source, and encoded prior to operation of the instrument.

In some embodiments, the matching process may not look for all possible matching opportunities within the entire image. The reference image is designed such that each point or group in the captured image can only possibly be a peer for a set of points laying along a line of specific width within the reference pattern. Restricting the area over which matches can occur may reduce the amount of processing power and processing time needed for the matching algorithm to complete its task and enhances the matching accuracy significantly. The reference pattern can also use a repetitive pattern, where a line can be repeated with a selected frequency without causing confusion and inaccurate results during the matching process.

Figure 6:
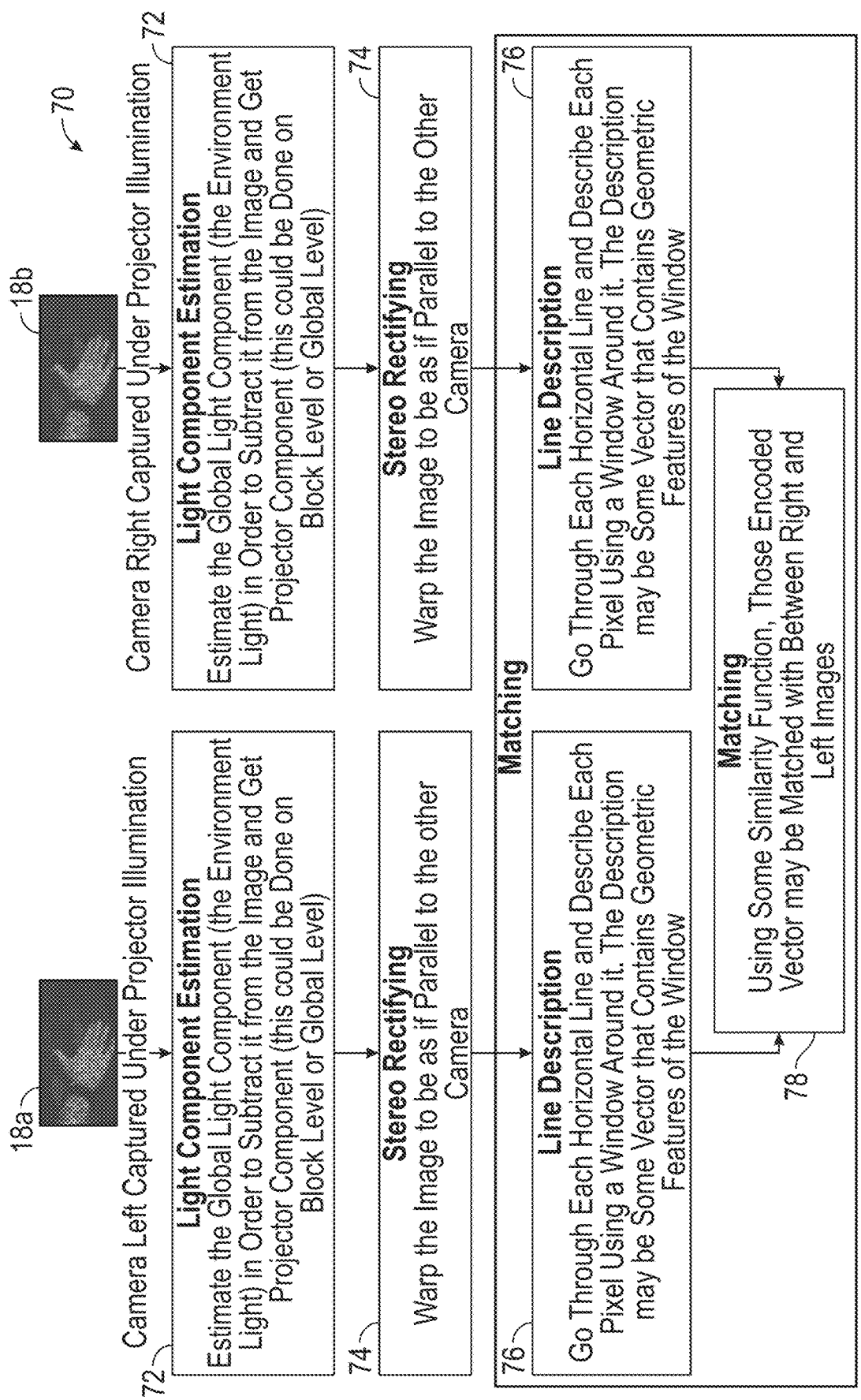
FIG. 6 is a flow chart illustrating another series of operations and calculations performed by an image reconstruction system to produce three-dimensional model(s) and/or measurement data in accordance with the present disclosure

FIG. 6 is a flow chart 70 illustrating a series of operations and calculations performed by the image reconstruction system 14b to produce three-dimensional model(s) and/or measurement data.

In a step 72, the system 14b performs light component estimation. Each camera 18b capture an image of the projected light on the tissue. The system 14b next produces an estimate of the global light component, also referred to as the environmental or background light intensity. The system 14b subtracts this background component from the captured image to (a) improve the contrast of the projected pattern reflected from the tissue under investigation, and (b) capture only the projected pattern illuminating the object for further processing in later stages. The estimation and elimination of the global light component can be performed on either a global level (one estimate for the entire captured image) or on a local level, with the light component estimation carried out in a series of segments or blocks within the image. Different background intensities may exist for the two cameras 18b, and the system 14b therefore processes the images from the cameras 18b independently.

In a step 74, the system 14b performs stereo rectifying. The system 14b performs an initial scan of the recorded images and locates the effective rows and columns of the image. The system then warps the image with processes including, but not limited to, rotation, scaling, and shifting, with the goal of aligning the recorded images of the two cameras 18b. The alignment process aims to make the rows of the two images parallel to each other and to likewise make the columns of the two images parallel to each other. The alignment process improves the performance of the matching process described below.

In a step 76, the system 14b performs line description. The system 14b proceeds through each horizontal line of the image and locates pixels or features of the projected pattern. The system 14b then describes each pixel of the projected pattern by surrounding the pixel with a window. The description of the pixel may include, but is not limited to, a vector that contains numerical representations of geometrical features of the window.

In a step 78, the system 14b performs matching. In particular, the system 14b aims to match a pixel or feature description from the image captured by the first camera 18b to a pixel or feature description from the image captured by the second camera 18b. The matching process may include, but is not limited to, the use of a similarity function to achieve best matches between descriptions and matching of vectors to within a minimum geometrical distance.

In some embodiments, the matching process may not attempt to search through the entire image of each camera 18b to find the best match between pixels. The alignment process performed during the line description step and the highly calibrated nature of the optical system limit the set of points in the second image, also called the reference image, which can potentially match the description of the considered point in the first image. The system 14b may need only to examine points within a horizontal slice through the second image. Limiting the area over which the matching process must search for the matching point may reduce the processing power needed by the matching process, decrease the processing time required to produce a model of the surrounding tissue, and enhance the accuracy of the matching process. Limiting the search area may also allow for the use of periodic patterns that repeat a unique pattern at each horizontal line without causing ambiguity or error in the matching process.

Figure 7:
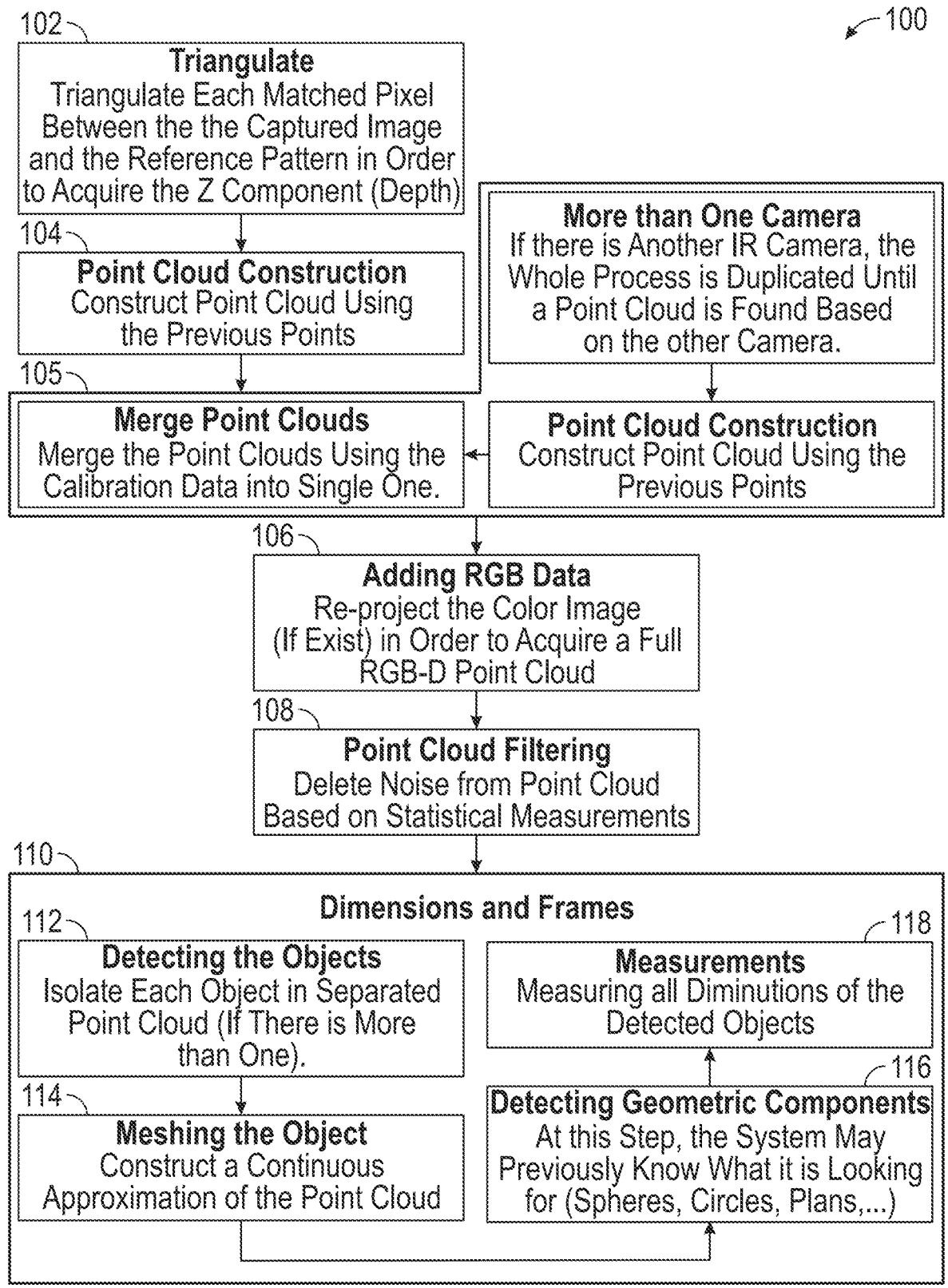
FIG. 7 is a flow chart of image reconstruction performed by medical scanning and mapping systems in accordance with the present disclosure.

FIG. 7 illustrates a flow chart 100 of image reconstruction performed by the systems 14a and 14b. For simplicity of description, the system 14a will be described herein in relation to image reconstruction unless otherwise specifically noted.

In a step 102, one of several accepted triangulation algorithms may be implemented to perform calculations to locate depth in each of the data points collected by the optical hardware system 12a and 12b. For the system 10b illustrated in FIG. 3, the aim is to match a pixel or feature description from the image captured by the first camera 18b to a pixel or feature description from the image captured by the second camera 18b. The matching process may include, but is not limited to, the use of a similarity function to achieve best matches between descriptions and matching of vectors to within a minimum geometrical distance.

In some embodiments, a depth learning algorithm may be implemented as a complement to or in place of the matching approach and triangulation algorithm. A depth learning algorithm uses regressive estimation of the depth through a process of labeling patches of the recorded image coupled with pattern recognition techniques. The depth learning algorithm removes the requirement for pattern matching and does not require stereoscopic techniques to accurately estimate depth. As a result, using a depth learning algorithm has the potential to increase the speed at which the system constructs 3D maps of the surrounding tissue, increase the resolution of the constructed model, and decrease the processing load required to construct the model. The overall robotic system performance may benefit from the use of the depth learning algorithm in several ways, including but not limited to reducing the delay between acquisition of the data by the cameras 18 and actions taken by the operator or control system to ensure safe and effective operation of the robotic surgical head.

In a step 104, a point cloud may be constructed for each coordinate set generated by an optical source-camera pair. The software then merges the set of point clouds into a single point cloud using available calibration data. Merging of point clouds involves the process of registration, wherein point clouds from different optical source-camera pairs are referred and aligned with a consistent frame of reference. The registration process establishes the relationships among point clouds and helps merge the multitude of point clouds into a single cohesive point cloud for modeling the object. If more than one camera 18 is used, the process may be duplicated until the point cloud is constructed as indicated by step 105.

In a step 106, red-green-blue (RGB) data may be added. If the visible light system used in the surgical procedure obtained color images of the tissue under investigation at the same time the infrared measurement system scanned the tissue, the system 14a may virtually project the merged point cloud onto the visual image. The purpose of this operation is to acquire a full red-green-blue (RGB) encoded point cloud that may allow construction of full color models of the scanned tissue. If color images do not exist, the software may skip this step and construct grey-scale models of the tissue in the later stages.

In a step 108, the point cloud may be filtered. The system 14a may utilize statistical measurements of the recorded data and known sources of electrical noise within the system 10a to perform targeted filtering of the point cloud in order to minimize or eliminate the noise from the point cloud data.

In a step 110, one or more models of the tissue may be formed. The one or more models may be used to detect features of interest and provide measurements of distances between points in the model and provide analysis of features of interest. The dimensioning and framing process includes four steps 112, 114, 116 and 118.

In step 112, the system 14a may detect objects of interest. The system 14a may construct separate point clouds focused on objects of interest to the surgeon, with each object described by an individual point cloud. The software may reconstruct models of the objects in later steps in addition to models for the larger area under investigation.

In step 114, the system 14a may mesh objects. The system 14a follows processes such as generalization, fusion, and optimization for constructing a continuous approximation of the point cloud. The accuracy of the continuous approximation depends to a large extent on the resolution of the optical hardware system 12a and the feature size of the projected pattern. High resolution and small feature size translate into a denser point cloud describing the scanned object, which subsequently results in a smoother approximation of the object within the constructed model.

In a step 116, the system 14a may detect geometric components. It should be noted that the following process may be generalized to the system 10 including the image reconstruction system 14 and is not limited to the embodiments of systems 14a and 14b. In some embodiments, the system 14 may utilize input from an operator regarding the shapes and geometries that the operator may want to highlight or identify within the continuous model of the point cloud generated in the previous step. For example, in colonoscopies, the operator may be interested in identifying polyps growing within the colon. Most polyps have predictable shapes and sizes, and the operator can input this information through an interface of the image reconstruction system 14. The image reconstruction system 14 may attempt to correlate components of the scanned model with the geometries of interest to identify and mark potential candidates for the operator to further examine either during the procedure or post-operatively.

In a step 118, the system 14 may generate measurements. The system 14 may utilize the model to provide measurement data to an operator. The operator may select specific objects for the system 14 to measure, may locate cursors or similar indicators within the model, or similar operations, and the system 14 may provide measurement data to the operator through one or more interface. The system 14 can also utilize the model to provide measurement to smart artificial intelligence systems that control and/or drive semi-autonomous and autonomous operation of the robotic surgical heads, including but not limited to autonomous driving of an endoscope in the colon or upper GI tract and stitching of hernias.

In general, outputs of the system 14 can include, but are not limited to: (1) a three-dimension model for display on a screen or other visual device for the purpose of further physical inspection by the surgeon and/or the surgical support team, and (2) an array or some other organization of numerical data used to construct the three-dimensional model, that the surgeon or surgical team can access in some form to make needed measurements between points on the surface.

In some embodiments, the systems 14a and 14b may be calibrated. For simplicity of description, the system 14a is described in detail herein. The calibration process may integrate the system 14a with the optical hardware system 12a. The calibration process may account for skewing of the projected pattern due to (a) the optical hardware system 12a illuminating the screen or tissue at an angle other than perpendicular to the plane of the screen or tissue; and/or (b) the angle of the optical source 16a with respect to the plane of the tissue or screen.

Figure 8:
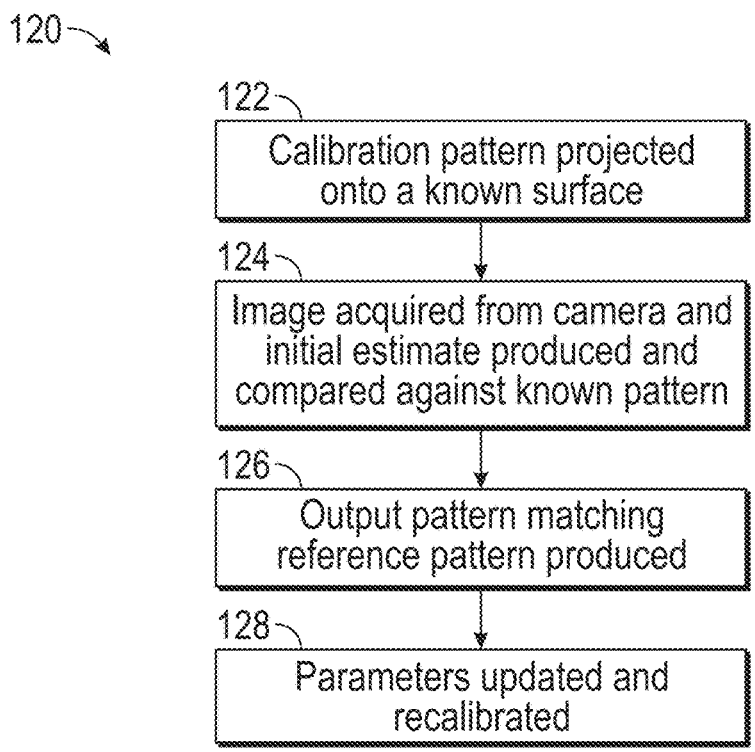
FIG. 8 is a flow chart of an exemplary calibration process for medical scanning and mapping systems in accordance with the present disclosure.

FIG. 8 illustrates a flow chart 120 of an exemplary calibration process. In a step 122, the optical source 16a and the pattern generator 28 project a calibration pattern onto a known surface. The surface can include, but is not limited to, a mono-color flat surface located at a distance expected in the target application, such as a screen or wall. The calibration pattern may include, but is not limited to, a checkerboard with alternating illuminated and non-illuminated squares. To obtain a specific measurement accuracy, the maximum feature size in the calibration pattern may not exceed the measurement accuracy value. For example, if the application requires measurement accuracy to 200 μm, the maximum feature size should be on the order of 50 μm. For the example of the checkerboard pattern, the sides of the squares in the pattern must be 50 μm or less in length.

In a step 124, the system 14a acquires the image from the camera 18a and produces an initial estimate of the received image. The initial estimate results from the system 14a may then be compared to the reference or known pattern. Corrections may be made to the calculations and other parameters within the algorithms and the system 14a generates a new estimate for comparison with the reference or known pattern. During this process, key parameters of the optical hardware system 12a, such as the distance between the camera 18a and the optical source 16a, the angle of the camera 18a, the angle of the optical source 16a, and/or the focal length of the optical source 16a may be loaded into and saved within the system 14a. In a step 126, the process may be repeated until the system 14a produces an output pattern that matches the reference pattern. Once the system 14a outputs an accurate reconstruction, all parameters of the optical hardware system 12a, the calculations, and the algorithms are loaded into permanent storage within the system 14a.

In a step 128, if the optical hardware system 12a employs an autofocus on the optical source 16a, the system 14a may know when the focal length of the optical source 16a changes and the new value of the focal length in order to recalibrate autonomously, and thus attain the desired accuracy with the new focal length parameter.

Figure 9:
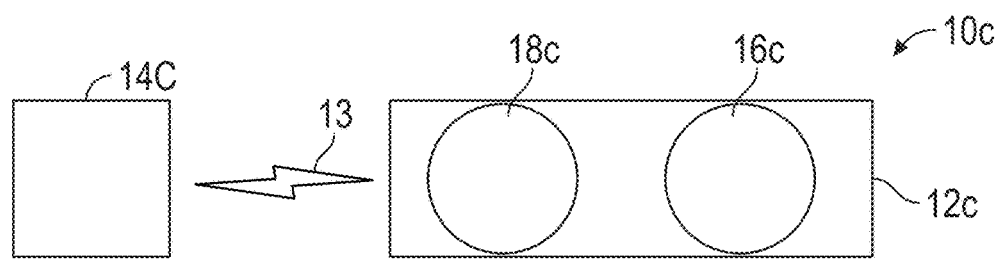
FIG. 9 is a block diagram of another exemplary medical scanning and mapping system of the present disclosure.

FIG. 9 illustrates another exemplary embodiment of a medical scanning and mapping system 10c. The medical scanning and mapping system 10c may include three main subsystems. First, an optical source 16c of infrared light may illuminate tissue under investigation. A continuous signal may modulate the optical source 16c at a high frequency and with a specific initial phase that acts as the base reference phase for measuring phase shifts. Second, a time-of-flight camera 18c sensitive to infrared light may record a set of at least four images, called sub-frames, of the optical illumination projected onto the surface of the tissue under investigation. Third, image reconstruction system 14c designed specifically to interpret the images and data output from the time-of-flight camera 18c reconstructs a 3D mapping or image of the illuminated tissue from the captured images and data. The properties of the components within each subsystem, the arrangement of the optical source 16c and time-of-flight camera 18c subsystems with respect to each other, the configuration of the complete system 10c within the tubular sleeve, and parameter selection within the image reconstruction system 14c may determine the performance of the system 10c in terms of lateral resolution, the depth of tissue for which the target resolution is achieved, the field of view over which the system 10c can make measurements, and the data made available to the surgeon or control systems for guiding the surgical or endoscopic procedure.

The optical source 16c may deliver significant optical power to the tissue under investigation without causing damage to the target tissue or the patient due to heating or interactions with high optical intensities. The optical source 16c may be a laser operating in the visible or infrared region of the optical spectrum. For example, the operating region may be in the near infrared (NIR) range between 700 nm and 1000 nm. Wavelengths include 780 nm, 808 nm, 850 nm, or 980 nm, as these wavelengths are available in commercial sources, provide maximum optical reflection from biological tissue, and may be sufficiently far from the visible light region of the optical spectrum to avoid interfering with the visible light camera used for robotic surgical procedures. An electrical signal varying periodically over a short time period may modulate light from the optical source 16c such that the properties of the light vary rapidly in time, corresponding to a high frequency modulation. For example, modulation frequency may be in the 50 MHz to 100 MHz range to simplify calculation of phase shifts by the software subsystems. The optical source 16c may provide sufficient power for the reflection from the tissue to be captured with sufficient contrast by the time-of-flight camera 18c, but low enough power to avoid damage to the patient or to saturate the sensors used in the camera 18c. The optical source 16c may produce illumination that lacks structure, including but not limited to uniform illumination intensity over space and deterministic spatial changes such as the Gaussian distribution of power with angular direction from the optical axis of the source common with laser light emitted from the output of optical fiber.

In one example, optical power may be delivered to the point of surgery via an optical fiber, fused array of fibers or similar waveguide strung through the tubular sleeve or endoscopic tool and terminating at the end of the tube. The end of the fiber may be formed as a flat surface or as a curved surface and may include one or more lenses to spread the light. A curved surface could include, but is not limited to, having a spherical or parabolic shape.

In another example, optical power may be delivered to the point of surgery via an extended source located at or near the end of the tubular sleeve or endoscopic tool, powered through electrical cable strung from an external power supply through the sleeve or endoscopic tool to the optical source 16c. Possible extended sources include, but are not limited to, any infrared LED with a broad emitting area, including an organic LED (OLED), that emit in the preferred wavelength range.

The time-of-flight camera 18c captures the optical intensity arriving at each pixel of the camera 18c after reflection from the tissue under investigation over a series of at least four frames and provides the image data as input into the image reconstruction system 14c. The camera 18c may utilize, but is not limited to, CCD or a similar technology, specifically technology that provides sensitivity to the preferred wavelengths of the source. The camera 18c may possess sensitivity only for the infrared wavelengths used in the optical source 16c. A band pass or low pass filter, which pass specific wavelengths while blocking others, may be placed in front of or included as part of the camera 18c to block optical power in specific parts of the spectrum to minimize noise. The camera 18c may have sufficient resolution in the recording surface to provide the image reconstruction system 14c with a number and density of samples of the captured image sufficient to meet the measurement needs of the intended application. Camera resolution depends on the size, density, and number of pixel elements contained with the light sensitive area of the camera 18c and on the frame rate of the camera 18c. The camera 18c should also have sufficient sensitivity to accurately record the light reflected by the tissue and directed back toward the camera 18c. Reflectivity of tissue is between 50-60%, depending on the type of tissue under investigation and thus the optical path between optical source 16c and camera 18c incurs losses in power.

The analysis software of the system 14c may convert the image data recovered from the light detecting array of the time-of-flight camera 18c and perform calculations to extract depth information and to construct a 3D mapping of the scene of interest. Images recovered from the light detecting array over four or more images, called sub-frames, provide information on the phase of the light signal detected at each pixel. The system 14c uses the image information, as well as information about the frequency and phase of the source modulation, the size and density of the light detecting array, and the position of the time-of-flight camera 18c with respect to the optical source 16c to perform calculations that determine the phase difference or shift between the received signal and the transmitted signal and converts the phase difference information into 3D position information about the scene captured by each pixel of the light detecting array. The software uses the 3D position information from all of the points to construct a 3D depth map of the entire image. Analysis software commonly comes packaged with the hardware of the time-of-flight camera 18c, and complete systems can be obtained from commercial vendors.

In some embodiments, elements of systems 10, 10a, 10b and 10c may be combined. Combinations and variants of systems 10, 10a, 10b, and 10c may provide additional information to increase accuracy, improve ability to detect objects of interest that one configuration may have difficulty in detecting but another configuration detects easily, and/or provide supplemental data to inform and/or determine control signals for autonomous or semi-autonomous operation of surgical and endoscopic instruments. Combinations and variants may include, but are not limited to, optical hardware system 12, 12a, 12b or 12c of one configuration combined with optical hardware system 12, 12a, 12b, or 12c of another configuration, the optical hardware system 12, 12a, 12b, or 12c of one configuration combined with the optical hardware system of more than one of the other optical hardware systems 12, 12a, 12b, and/or 12c, the optical hardware system 12a including two cameras 18 (e.g., cameras 18b), camera 18a combined with multiple optical sources 16a, camera 18b combined with multiple optical sources 16b, multiple optical sources 16a combined with multiple cameras 18a, multiple optical sources 16b combined with multiple cameras 18b, and/or the like.

Figure 10:
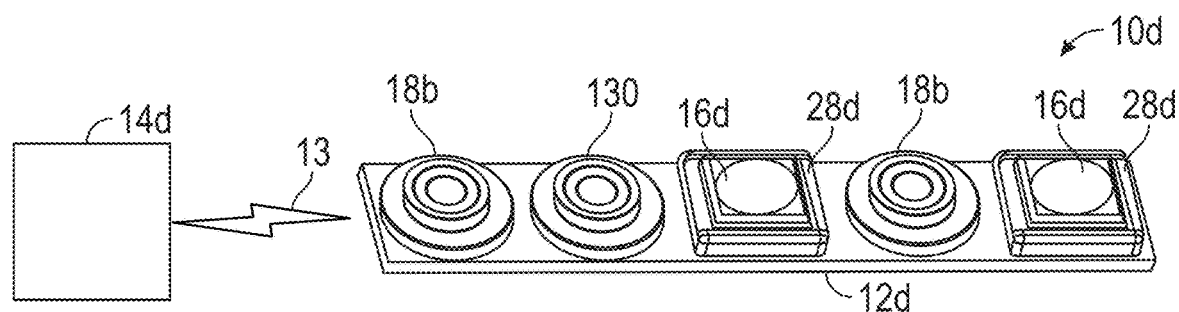
FIG. 10 is a block diagram of another exemplary medical scanning and mapping system of the present disclosure.

FIG. 10 illustrates an exemplary embodiment of a system 10d having two or more cameras 18d and two or more optical sources 16d. The system 10d includes two infrared cameras 18b, two pattern generators 28d, two optical sources 16b and a visible camera. The use of multiple cameras 18d placed at different angles may increase the ability to detect light illuminating folds, crevices, and/or similar structures that might be shadowed from the view of one camera 18d, but visible from the viewpoint of the other camera. Multiple cameras 18d may also provide overlapping FOVs and thus overlapping data sets within the software of the image reconstruction system 14d which can improve the process of assigning an accurate 3D position of each part of the tissue under investigation and increase accuracy of the output 3D model and measurements. The cameras 18d can be located at different distances from the optical source 16d, providing varying levels of resolution along the depth dimension, allowing different source-camera pairs to focus on detecting features of different sizes.

Use of multiple optical sources 16d may also illuminate the tissue at different angle to illuminate fold, crevices, and similar structures that might otherwise escape illumination and thus not be captured by the cameras or modeled by the image reconstruction system 14d. Different optical sources 16d can project different patterns over the same area, allowing the system to take advantage of the strengths of the different patterns to improve the overall reconstructed image. The optical sources 16d can be located at different distances from the cameras 18d, providing varying levels of resolution along the depth dimension, allowing different source-camera pairs to focus on detecting features of different sizes.

For the systems or combination of systems 10, 10a, 10b, 10c or 10d in which the user can capture the image projected by a single optical source 16 using multiple cameras 18, 18a, 18b, 18c or 18d, or where the user can capture the images from multiple optical sources 16, 16a, 16b, 16c or 16d using a single camera 18, 18a, 18b, 18c, or 18d, or some combination thereof, the analysis process within the software is carried out for each combination of optical source 16, 16a, 16b, 16c, or 16d and camera 18, 18a, 18b, 18c, or 18d, (herein referred to as 'an optical source-camera pair') investigated or utilized by the optical hardware system 12, 12a, 12b, 12c, or 12d. For example, for the software described in systems 10a, 10b and 10c, the entire analysis process may be repeated for each source-camera pair investigated. The triangulation algorithm produces a unique set of points and corresponding coordinate data for each source-camera pair, and then passes all point/coordinate sets to the remaining steps of the image reconstruction process to build and measure the 3D model. For the systems 10, 10a, 10b, 10c and 10d, a similar process would occur, wherein the software would combine the 3D position data produced by analysis of data from each pair of camera 18 and optical source 16 to build and measure the 3D model.

After constructing a three-dimensional spatial model of one segment of the surgical or endoscopic environment, each system 10, 10a, 10b, 10c or 10d can operate in one of two ways, and can use both methods of operation for some applications.

In the first method of operation, the surgeon or endoscopic operator moves the optical hardware system 12, 12a, 12b, 12c or 12d through the environment taking a series of independent images. In this method, the software constructs and stores three dimensional models and spatial data for each image, but does not attempt to stitch the individual models together into a larger whole or to locate each image within the larger surgical or endoscopic environment. This first method of operation may require no additional sensors to provide feedback regarding the positioning and location of the optical hardware system 12, 12a, 12b, 12c or 12d within the surgical or endoscopic space. The method can use data collected from the images to provide control signaling needed to implement autonomous or semi-autonomous operation of robotic surgical and endoscopic systems.

In the second method of operation, the surgeon or endoscopic operator may move the optical hardware system 12, 12a, 12b, 12c or 12d through the environment with the intention of mapping the entirety of the surgical or endoscopic environment or section of high interest within the surgical or endoscopic environment. The software may require additional data from the optical hardware system 12, 12a, 12b, 12c or 12d in order to stitch together individual images into a cohesive and accurate model of the entire environment. For example, additional data may include a minimum level of spatial overlap between the recorded images as the optical scanning hardware moves through the environment and sensors that record the orientation of the scanning head and the location of the scanner within the environment or patient. The additional sensors may include sensors integrated within the same instrument that contains the optical hardware system 12, 12a, 12b, 12c or 12d (such as an inertial measurement unit (IMU) to define the orientation of the optical scanner), sensor arrays within the surgical or endoscopic environment independent from the scanning instrumentation, and/or sensor arrays located externally to the surgical or endoscopic environment that detect signals which allow the software to locate the position of the optical hardware system 12, 12a, 12b, 12c or 12d within the patient. The additional information and the cohesive three-dimensional mapping of the environment may provide sufficient information to generate control signaling needed to implement autonomous or semi-autonomous operation of the robotic surgical and endoscopic systems, especially in situations where the endoscopic instrument needs to change shape in the areas behind the scanning head. Mapping functionality may also support a number of additional functions and applications, such as detection and mitigation of loops during colonoscopy.

The medical scanning and mapping system 10, 10a, 10b, 10c, or 10b may provide the size, accuracy, and functionality needed to advance applications in laparoscopic and robotic surgery, particularly minimally invasive surgery, and in endoscopic procedures such as colonoscopy. The small size of the optical hardware system 12, 12a, 12b, 12c or 12d may allow for implementation of the scanner either on a separate instrument inserted in parallel with the instruments used in the surgical or endoscopic procedure, or integrated directly within the surgical instrumentation or endoscope hardware. The submillimeter or millimeter accuracy of the system 10, 10a, 10b, 10c, or 10d in reconstructing the surgical or endoscopic environment improves the operator's ability to detect features of interest, perform accurate measurements of such features, and improve positioning and movement of the surgical or endoscopic tools. The functionality of the system 10, 10a, 10b, 10c, or 10d may enable advanced control, augmented visualization, and autonomous or semi-autonomous operation of the surgical or endoscopic procedure.

The system 10, 10a, 10b, 10c or 10d may at least impact the medical scanning and mapping system in common applications including, but not limited to endoscopy, laparoscopic and robotic surgical application. In laparoscopic and robotic surgical applications, the surgeon inserts the surgical tools through small holes or incisions and relies on optical source 16, 16a, 16b, 16c or 16d and camera(s) 18, 18a, 18b, 18c or 18d, respectively, inserted through the same or other incisions to visualize the surgical space and direct the instruments to perform the procedure. In the medical scanning and mapping system 10, 10a, 10b, 10c or 10d, the surgeon can pursue two options for delivering the optical hardware system 12, 12a, 12b, 12c or 12d, respectively, to the surgical site. In the first option, the surgeon inserts a separate instrument containing the optical hardware system 12, 12a, 12b, 12c or 12d, in addition to the other tools and instruments currently used to perform the procedure. In the second option, the surgeon uses a modified tool that integrates the optical hardware system 12, 12a, 12b, 12c or 12d with an existing instrument, such as the visual light source and two dimensional or three dimensional camera system currently used to view the surgical environment. In either option, the image reconstruction system 14 of the medical scanning and mapping system 10, 10a, 10b, 10c, or 10d processes images as described above to provide information to the surgeon or to allow the surgical system to operate in an autonomous or semi-autonomous manner. The image reconstruction system 14 may be integral to the optical hardware system 12, 12a, 12b, 12c or 12d, and as such, in some embodiments, at least a portion of the image reconstruction system 14 may be within a patient's body during use. In some embodiments, the entire image reconstruction system 14 may be external to a patient's body during use of the system 10, 10a, 10b, 10c or 10d.

At the basic level, the image reconstruction system 14 provides an operator with the ability to perform highly accurate, real-time measurements of the three-dimensional surgical environment. Examples include, but are not limited to, measurements of the herniated area for determining patch dimensions and the placement of stitches when sewing up incisions. At the next level of functionality, the system 14, 14a, 14b, 14c, or 14d can utilize the data to identify the three-dimensional position, orientation, and movement of surgical instruments within the surgical environment for a variety of purposes. Examples include, but are not limited to, providing warnings or alarms when the surgical instruments endanger surrounding tissue, especially blood vessels and organs and identifying the position and orientation of the camera(s) 18, 18a, 18b, 18c or 18d to help the operator locate features and mentally orient themselves during the procedure. The image reconstruction system 14 can augment the imagery provided by the visible light systems to enhance the amount of information available to the operator during the procedure. Examples include, but are not limited to, providing measurement information directly on a feature of interest, identifying or highlighting features within the environment, and placing virtual targets on positions to guide suturing, cutting or incisions made by the surgeon. The detailed information produced by the system 14, 14a, 14b, 14c, or 14d may allow for the generation of control signals to guide the robotic and laparoscopic systems to perform surgical procedures or parts of procedures in an autonomous or semi-autonomous manner. Examples include, but are not limited to, precise suturing for closing incisions or hernias, and guiding instruments to perform precise or difficult movements.

In endoscopic applications, including colonoscopy, the surgeon or operator inserts a flexible tool into an opening such as the anus or the throat and steers the tool to observe patient health and to possibly perform small surgical procedures to address problems observed during the procedure. In the medical scanning and mapping system 10, 10a, 10b, 10c or 10d, the operator can pursue two options for delivering the optical hardware system 12, 12a, 12b, 12c or 12d, respectively to the same locations and the visible light-based endoscope. In the first option, the optical hardware system 12, 12a, 12b, 12c or 12d consists of a separate tool that attaches to the head of the endoscope in some manner, effectively acting as an accessory added onto the base tool. In the second option, the optical hardware system 12, 12a, 12b, 12c or 12d each can integrate directly into an endoscopic tool, effectively creating a new endoscopic tool with greatly increased functionality. In either option, the system 14, 14a, 14b, 14c, or 14d of each medical scanning and mapping system 10, 10a, 10b, 10c, or 10d, respectively, may process images as described previously to provide information to the endoscopic operator or to allow the endoscope to operate in an autonomous or semi-autonomous manner. For example, during a colonoscopy procedure, at the basic level, the system 14, 14a, 14b, 14c, or 14d can utilize measurement and imagery data to assist the operator in detecting the existence of a polyp within the patient's colon and in measuring the size and dimensions of the polyp, both of which prove critical in identifying and mitigating problems that can later lead to colon cancer. If the operator decides to cut a polyp during the colonoscopy procedure, the system 14, 14a, 14b, 14c or 14d can provide the imaging data to determine which tool the operator should use to cut the polyp and to provide measurements and positioning data to properly guide and position the tool to ensure the operator removes the entire polyp. At higher levels, the system 14, 14a, 14b, 14c or 14d can assist the operator in identifying the formation of loops within the colon, provide three-dimensional mapping of the patient's colon that the operator or the patient's doctor can use to track changes in health over time, and to provide extensive documentation of the entire colonoscopy procedure for later evaluation and analysis. The detailed information produced by the system 14a, 14b, 14c or 14d may allow for the generation of control signals to guide the endoscope through the procedure in either an autonomous or semi-autonomous manner, or to generate augmented displays which assist the operator in guiding current endoscopic tools during a procedure. The autonomous, semi-autonomous, and augmented operating modes may allow, for example, surgeons and other specialists not specifically trained in gastroenterology to perform colonoscopy procedures at a high level and meet the increasing demand for using colonoscopy for both preventative and treatment purposes.

Additional applications for the system 10, 10a, 10b, 10c or 10d are contemplated. In one example, the system 10, 10a, 10b, 10c or 10d may be used to construct a 3D model of the scanned tissue, which can contribute to augmented artificial intelligence navigation guidance for the surgeon or endoscopic operator and further applications in surgical simulation.

In another example, the system 10, 10a, 10b, 10c or 10d may provide measurements of key distances or features within the scanned volume, including lateral, perimeter, area, and depth measurements, including the circumference and shape of herniated tissue to ensure proper patch overlap. In hernia repair surgeries and similar procedures, the surgeon selects the correct-sized patch needed to perform the repair. Proper size selection requires accurate measurement of both the lateral dimensions and the depth dimensions of the area into which the patch will be placed. The system 10, 10a, 10b, 10c or 10d may provide these measurements to the operator, and the interface can allow the operator to interact virtually with the target area to ensure that the selected patch will fit before continuing the procedure.

In another example, the imaging and measurement capabilities of the system 10, 10a, 10b, 10c or 10d can provide input to some form of alarm or warning system that notifies the operator or surgeon when the robotic surgical instrument approaches too closely tissue that may suffer damage from the instrument, and when the orientation, angle, and/or placement of the surgical instrument within the patient is incorrect. Such an alarm could prevent accidental injury to the patient that could potentially occur during the surgical procedure.

In another example, the system 10, 10a, 10b, 10c, or 10d can process the scanner data and independently generate control signals that direct a visible imaging camera to track along with the movement of the surgeon's tools. The system 10, 10a, 10b, 10c or 10d can implement object recognition algorithms to identify one or more surgical tools within the surgical environment and subsequently generate control signaling that leverages interconnections between the software and hardware components of the system to adjust the position and angle of the system to keep the surgical tools within the central portion of the scanned area. As a result, the surgeon can continue operating without stopping to reposition the camera, reducing the duration of the surgery, allowing the surgeon to maintain concentration on the surgical procedure, and minimizing the possibility of errors inherent in the continual switching back and forth between control of the imaging system and control of the surgical instruments.

In another example, the system 10, 10a, 10b, 10c or 10d can provide options for assisting the surgeon in quickly and confidently making precise cuts. One possible option utilizes object recognition algorithms and real-time processing of scanned images to track the position of the cutting tool with time and providing real-time data on length of the cut or the position of the cutting tool with respect to the edge of the diseased area. The system 10, 10a, 10b, 10c or 10d may include methods for the surgeon to provide input or otherwise signal to the software when to begin measuring the movement of the surgical instrument. In another example, measurement data may overlay from the scanner onto the visual image of the surgical space provided by the visible-light camera, effectively creating an augmented reality operating environment. Possible interactions between the surgeon and the system 10, 10a, 10b, 10c, or 10d may include, but are not limited to, (1) planning the cut graphically on the display using the measurement data to ensure the correct length or distance, and then effectively cutting along the line, and (2) providing real-time measurement data on the screen next to the tracked instrument to allow the surgeon to adjust or end the procedure with precision. These and other possible options would enable the surgeon to become adept at making precision cuts or incisions without prolonged times for training or gaining experience, other than the expected short training period in operation of the software interface.

Newer robotic systems utilize a variety of technologies to steer the surgical head around tissue and anatomy to make minimally invasive surgery a real option for procedures that typically require invasive procedures to perform. For example, flexible robotic endoscopes can be driven by the operator or surgeon through the mouth to examine and perform procedures on the throat and upper respiratory systems, or driven along the colon to perform a colonoscopy. Another example includes the sewing of incisions using robotic manipulators instead of the surgeon's hands to minimize contamination and maintain sterilization of the incision site. The system 10, 10a, 10b, 10c and 10d can provide imagery and measurement data of sufficient precision and detail to support development of robotic systems with limited to full autonomous operating capabilities. The system 10, 10a, 10b, 10c or 10d can also include a visible light system that allows the operator to see what the system 10, 10a, 10b, 10c, or 10d sees and observe the movement of the system throughout the surgery or procedure. In the system 10, 10a, 10b, 10c or 10d, the head of the surgical instrument or endoscope utilizes a combination of proximity sensors and optical scanners place along the side or at the front of the head to scan the environment in all directions around and in front of the instrument head and construct a three dimensional model of the environment and embed measurement data within the model. The system 10, 10a, 10b, 10c or 10d can utilize the resulting model and measurement data to operate at different levels of autonomy during the surgery or procedure. In a semi-autonomous level of operation, the operator retains primary control of the robotic systems, and the system 10, 10a, 10b, 10c, or 10d can provide alarms to warn of potential dangers or errors that could lead to injury to the patient, temporarily take control of the robotic system to avoid such dangers, and provide imagery that assists the operator during the task. In a fully autonomous level of operation, the system 10, 10a, 10b, 10c or 10d may exert primary control over the robotic systems, using the 3D model and measurement data as inputs to control and feedback systems that utilize artificial intelligence techniques to direct the movements of the robotic surgical instrument autonomously, within a set of parameters dictated by the operator or the procedure. The operator would retain the ability to override or pause the autonomous operation to inspect something of interest to the operator or to perform some operation outside of the main procedure, and then allow the autonomous operation to continue.

For example, a robotic hernia surgery typically requires sewing of the hernia within the abdomen using the robotic systems. In a semi-autonomous mode of operation, the system 10, 10a, 10b, 10c, or 10d would provide a three-dimensional mapping and measurement of the space within the abdomen, including the section of tissue to be sewn together. The mapping may provide the operator with information on the range of movements possible without injuring the patient, the location of blood vessels and tissues the operator must avoid, and continually update imagery of the hernia throughout the surgery, so that the operator can ensure that all parts of the herniated area are sewn correctly. The system 10, 10a, 10b, 10c or 10d may warn the operator through messages, sound, or other means when movement of the robotic manipulators threatened to cause injury. In a fully-autonomous mode of operation, the system 10, 10a, 10b, 10c or 10d may utilize the three-dimensional mapping and measurement to accurately locate the target site for sewing, monitor the movements of the robotic systems performing the sewing operation, and monitor the sewing site to allow the system and the operator to verify that the sewing process is correct and complete. In some embodiments, the operator could override the autonomous systems to provide corrections, modify operations, or inspect the work of the robotic systems as needed.

In another example, endoscopy procedures may require that the endoscope traverse a twisting and sometimes circuitous path without scraping or otherwise damaging tissue at the bends in the path. A colonoscopy may require the endoscope to navigate sharp bends in the colon. An upper endoscopy may require the endoscope to navigate bends through the mouth, trachea, and into the esophagus and continue to successfully navigate the bends as the head of the endoscope moves forward. In either autonomous or semi-autonomous modes of operation, the system 10, 10a, 10b, 10c or 10d may generate a model or map of the surrounding tissue along the endoscope's route. The operator or control system can utilize the map to control, not only the head of the endoscope, but also the entire body of the endoscope, ensuring that the shape of the endoscope body conforms to the path through the patient at all times and thus minimizing the chance of causing damage to the patient. The whole endoscope therefore moves autonomously even though the system 10, 10a, 10b, 10c or 10d or optical hardware system 12, 12a, 12b, 12c or 12d may be located only in the head of the endoscope.

FIGS. 11-17 illustrate exemplary embodiments of systems 10, 10a, 10b, 10c or 10d for use within a body. For simplicity in description, the medical scanning and mapping systems 10 is described herein with reference to such embodiments; however, any of the systems 10a, 10b, 10c and 10d may be used in addition to or in place of unless otherwise indicated. It should be noted that the image reconstruction system 14, shown in FIG. 1, of each system 10, may be external to a patient's body during use or at least a portion may be combined into hardware of each system and positioned internal to the patient's body during use. Additionally, in some embodiments, multiple systems 10 within one device may include a single image reconstruction system 14.

Figure 11:
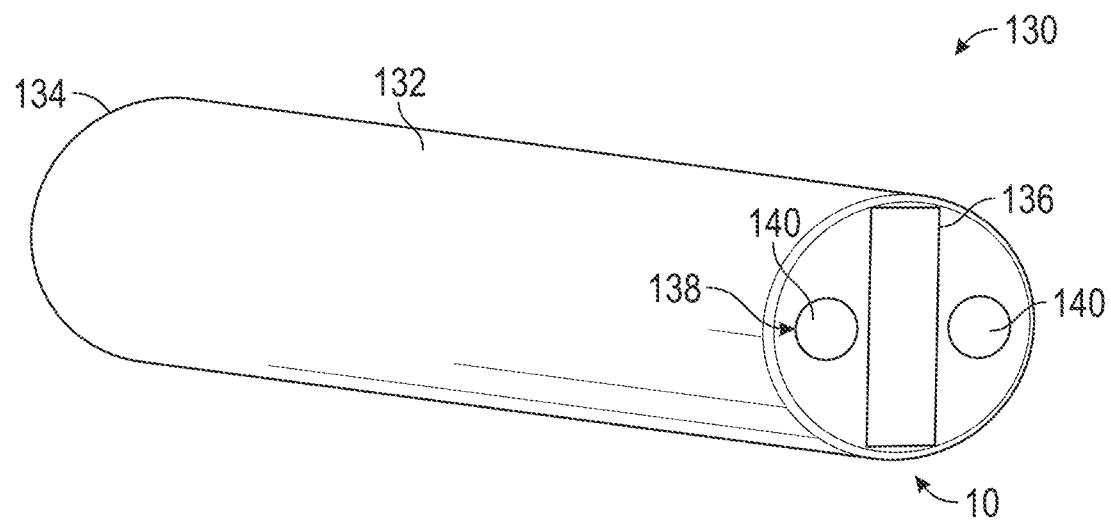
FIG. 11 is a perspective view of an exemplary embodiment of an integrated system having at least one medical scanning and mapping system in accordance with the present disclosure.

FIG. 11 illustrates an exemplary embodiment of an integrated system 130. The integrated system 130 includes a tubular sleeve 132 having a first end 134 and a second end 136. The tubular sleeve 132 includes a visible light system 138 and the medical scanning and mapping system 10 positioned on the second end 136 of the tubular sleeve 132 such that all optical source/camera pairs are positioned out of the second end 136 of the tubular sleeve 132. The visible light system 138 may use at most two cameras 140, situated along the horizontal axis, with illumination tubes surrounding the cameras 140. Given the current diameter of the tubular sleeve 132 and a typical size for components of visible light system 138, the medical scanning and mapping system 10 can fit along the vertical axis of the tubular sleeve 132, as shown in FIG. 11 for a typical robotic surgery application.

Figure 12:
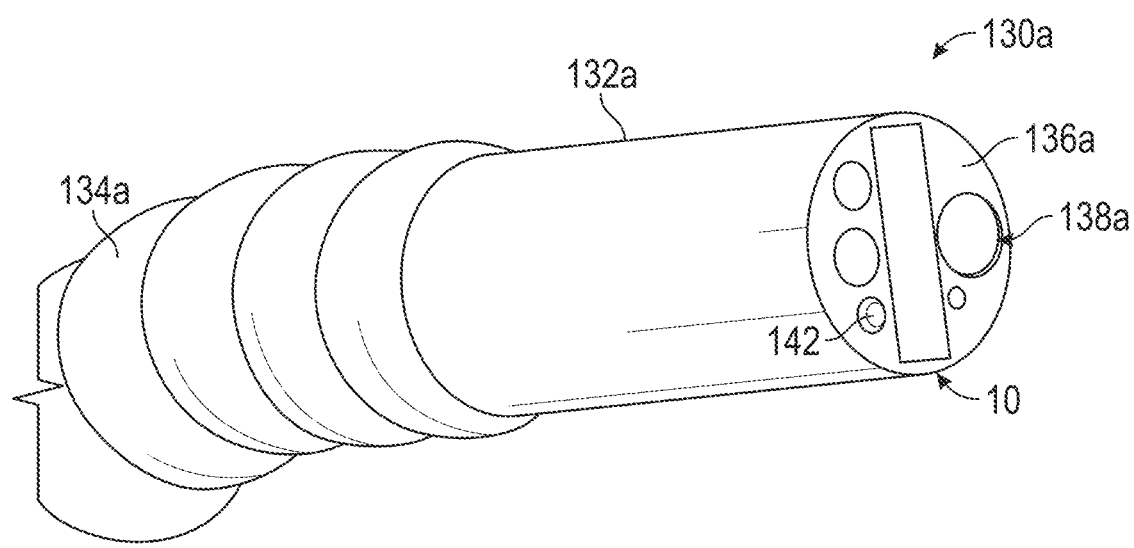
FIG. 12 is a partial perspective view of another exemplary embodiment of an integrated system having at least one medical scanning and mapping system in accordance with the present disclosure.

FIG. 12 illustrates another exemplary embodiment of an integrated system 130a used in colonoscopy procedure. The integrated system 130a includes a tubular sleeve 132a having a first end 134a and a second end 136a. The tubular sleeve 132 includes a visible light system 138a and the medical scanning and mapping system 10 positioned on the second end 136a of the tubular sleeve 132a such that all optical source/camera pairs point forward out of the second end 136 of the tubular sleeve 132a. The maximum possible FOV in this configuration embodiment is 180°. One or more proximity sensors 142 may be integrated at any position within the second end 136a of the tubular sleeve 132a. Note that when multiple medical scanning and mapping systems 10, 10a, 10b, 10c and/or 10d are available at the second end 136a of the tubular sleeve 132a, depth can be measured at different resolutions, if desired, by sequentially utilizing different scanning system 10, 10a, 10b, 10c and/or 10d. This ability to vary resolution would allow the surgeon or operator to selectively measure or model or identify large scale objects or to acquire more detail on smaller objects or features within the larger scene.

Figure 13A:
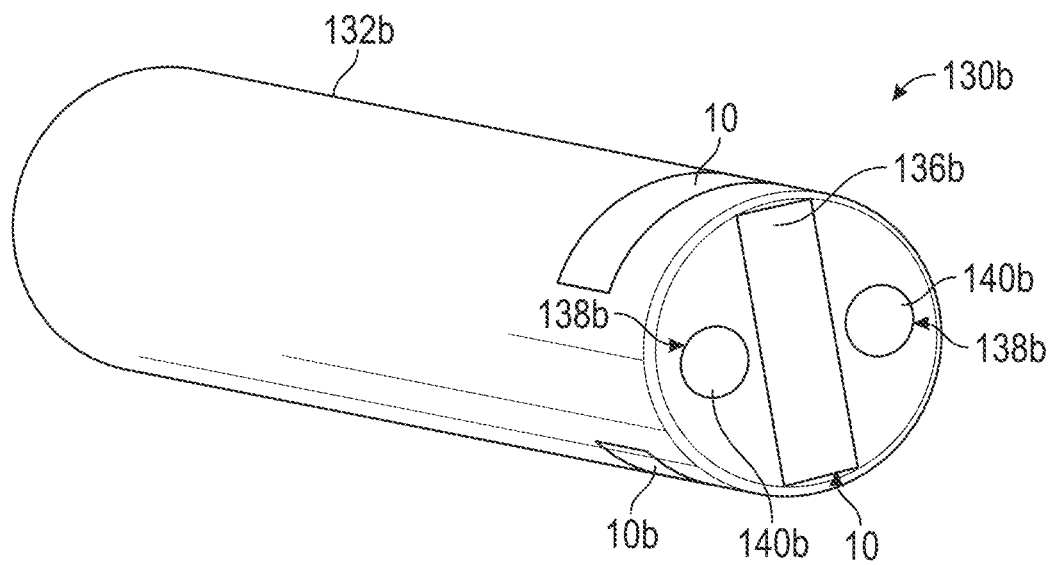
FIGS. 13A and 13B are perspective views of exemplary embodiments of integrated systems having at least two medical scanning and mapping systems in accordance with the present disclosure.
Figure 13B:
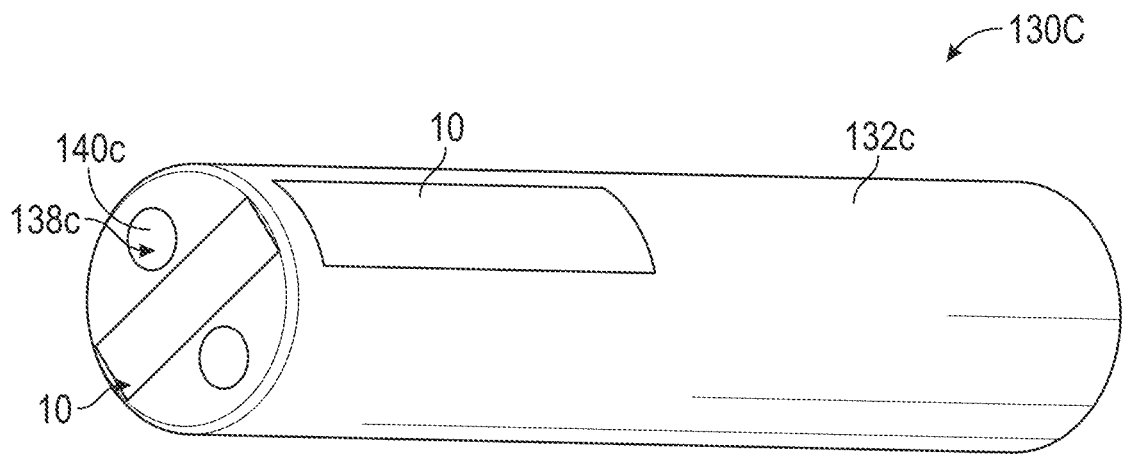

FIG. 13A illustrates another exemplary embodiment of an integrated system 130b having a visible light system 138b positioned within a tubular sleeve 132b similar to the integrated system 130a of FIG. 12. The visible light system 138b may use cameras 140b positioned on a second end 136b of the tubular sleeve 132b. The integrated system 130b includes at least two medical scanning and mapping systems 10 about the circumference of the tubular sleeve 132b: one system 10 oriented in upward direction and one system 10 in the lower direction. For example, multiple systems 10 may face outward from sides of the tubular sleeve 132b, and positioned perpendicular to the axis of the tubular sleeve 132b. Each system 10 may have a FOV as close to 180° as possible, for the tubular sleeve 132b used in robotic surgery. The tubular sleeve 132b used in endoscopy procedures, such as colonoscopies, could include a similar configuration. Using a FOV near 180° may allow the patterns from adjacent sources to nearly overlap. The second medical scanner and mapping system 10 may be oriented around the circumference of the tubular sleeve 132b, as shown in FIG. 13A, along the length of the tubular sleeve 132b as shown in FIG. 13B, (i.e., an integrated system 130c having a visible light system 138c with at least one camera 140c, the medical scanning and mapping system may be facing outward from the side of the tubular sleeve 132c and oriented parallel to the axis of the tubular sleeve 132c), or some combination of the two options wherein one or more medical scanning and mapping systems 10, 10a, 10b, 10c, or 10d lie along the length of the tubular sleeve 132b and/or one or more medical scanning and mapping systems 10, 10a, 10b, 10c, and/or 10d are oriented around the circumference of the tubular sleeve 132b. Any overlap between the FOVs of the medical scanning and mapping systems 10, 10a, 10b, 10c, and/or 10d may assist the systems 14, 14a, 14b, 14c, or 14d by providing anchor points for stitching together the measurements from individual medical scanning and mapping systems 10, 10a, 10b, 10c, or 10d. Overlap may also be realized by (a) using three or four medical scanning and mapping systems 10, 10a, 10b, 10c, and/or 10d with a smaller FOV or (b) having the surgical operator rotate the tubular sleeve 132b to scan or measure the entirety of the tissue or only areas of interest targeted by the operator, as demonstrated in FIG. 13B. Proximity sensors 142 may be integrated at any position respect to the medical scanning and mapping system 10, 10a, 10b, 10c, or 10d.

Figure 14:
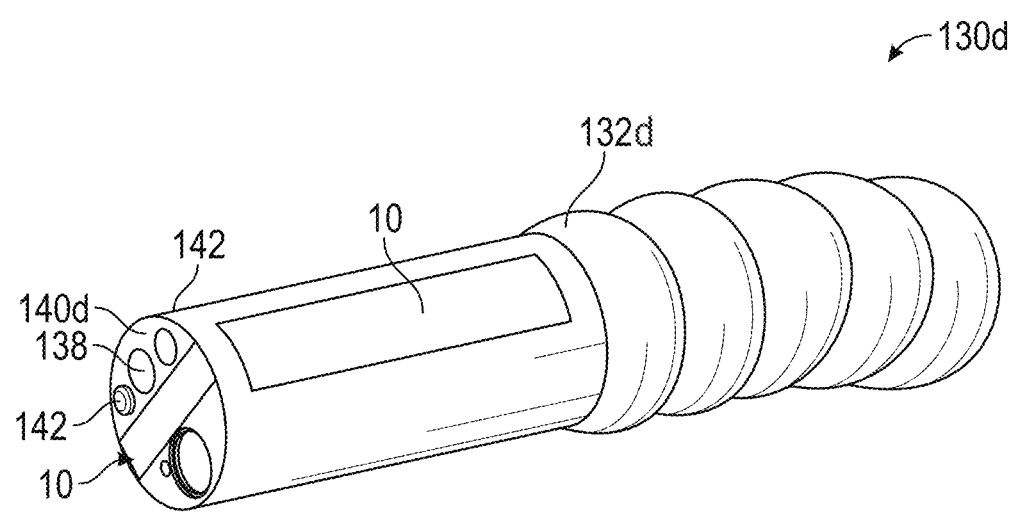
FIG. 14 is another exemplary embodiment of an integrated system having at least two medical scanning and mapping systems in accordance with the present disclosure.

FIG. 14 illustrates another exemplary embodiment of an integrated system 130d. The integrated system 130d may include one or more camera 140d and one or more medical scanning and mapping systems 10 in the tubular sleeve 132d or colonoscopy tool having one or more optical source-camera pairs positioned from the side wall of tubular sleeve or colonoscopy tool and one or more scanning systems 10 oriented from a second end 136d of the tubular sleeve 132d or colonoscopy tool, as shown in FIG. 14. Measurement and model construction of a hemispherical surface area or larger surface area of tissue can be realized. Scanning systems 10 may be distributed in any combination of configurations. Proximity sensors 142 may be integrated at any position with respect to the scanning system.

Figure 15A:
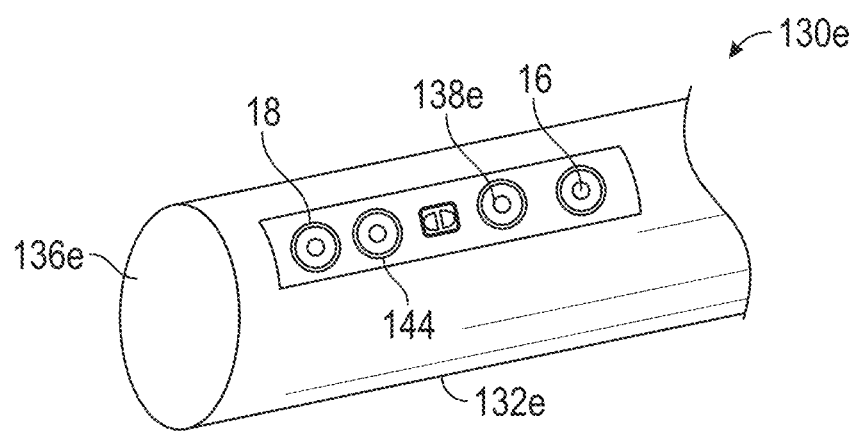
FIGS. 15A and 15B are partial perspective views of exemplary embodiments of an integrated systems having at least one visible light source and one or more cameras having visible light sensitivity.
Figure 15B:
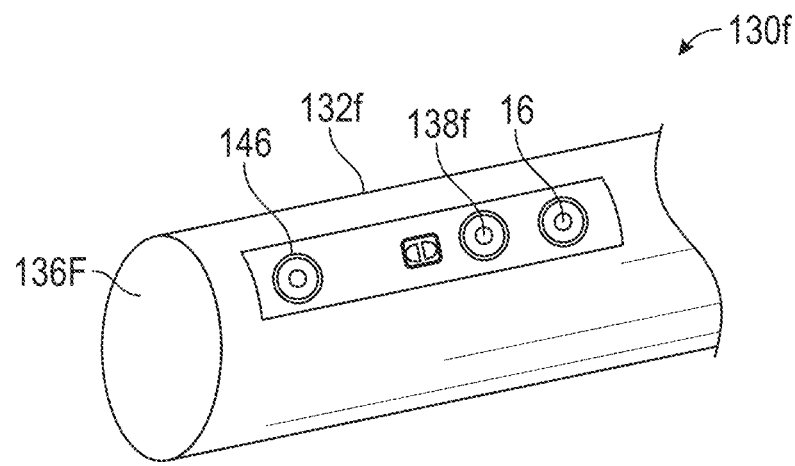

FIGS. 15A and 15B illustrates exemplary embodiments of an integrated system 130e and integrated system 130f, respectively. The integrated system 130e includes a visible light source 138e and one or more cameras 144 having visible (e.g., RGB) light sensitivity. In some embodiments, the medical scanning and mapping system 10 may include one or more optical sources 16 of the optical hardware system 12 having infrared light with the optical source 16 positioned outward from a side of a tubular sleeve 132e as shown in FIG. 15A. In some embodiments, the integrated system 130e may additionally include a forward facing medical scanning and mapping system 10, 10a, 10b, 10c, and/or 10d positioned on a second end 136e of the tubular sleeve 132e. The visible light source 138e may include, but is not limited to, a flash or illumination-based visible light source. The camera 144 may include, but is not limited to, a visible light sensitive camera independent of the infrared sensitive camera 18 as shown in FIG. 15A, or a single camera 146 with sensitivity in both the visible (RGB) and infrared regions as shown in FIG. 15B (having the single camera 146 and visible light source 138*f* within the tubular sleeve 132*f* positioned a distance from an end 136*f*). The visible light source 138*e* and camera 144 components may be integrated with the medical scanning and mapping system 10 to allow capture of visible light images of the tissues scanned by the system 10. Methods for capturing both visible and infrared images include, but are not limited to, simultaneous recording of images from one or more cameras 18, 144 and/or 146 or sequenced illumination, with the tissue illuminated by first one wavelength range and then another, and collection of data from one or more cameras 18, 144 and/or 146 sensitive at the wavelength used during each illumination periods. Uses of these images include, but are not limited to, visual records of a surgical procedure or the health of patient tissue for future reference or analysis, and integrating with images and measurements obtained from the medical scanning and mapping system 130*e* or 130*f*.

Figure 16:
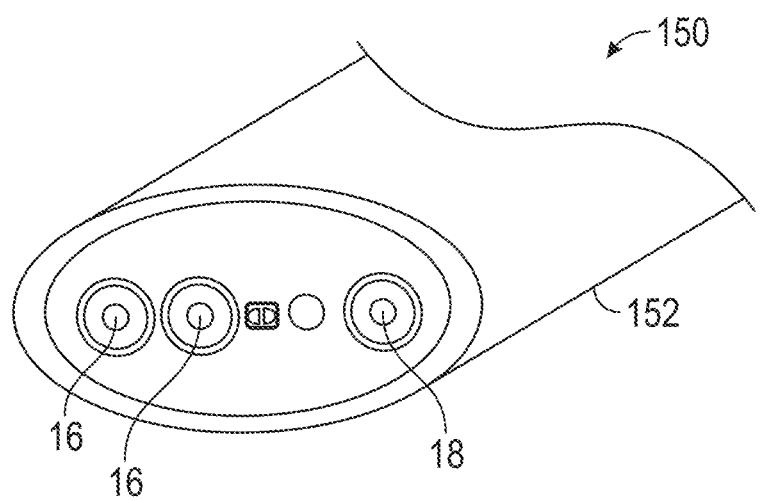
FIG. 16 is a partial perspective, end view of an exemplary medical scanning and mapping systems formed as a unitary system.
Figure 17A:
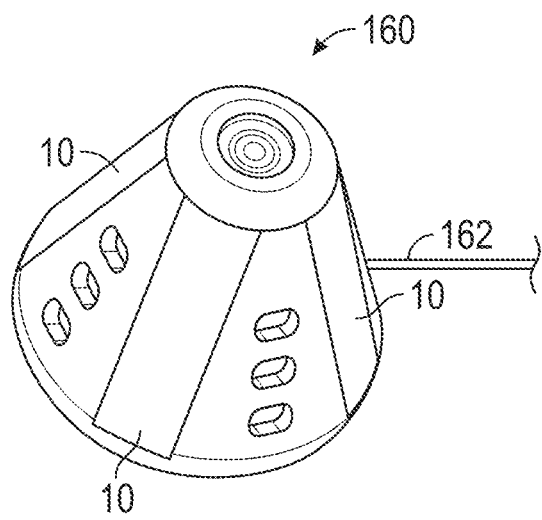
FIGS. 17A-17D illustrate exemplary medical scanning and mapping systems provided on exemplary platforms configured to be positioned within a patient and operated independently of a tubular sleeve in accordance with the present disclosure.
Figure 17B:
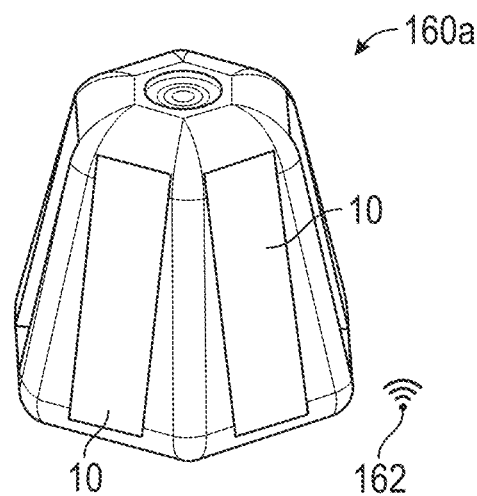
Figure 17C:
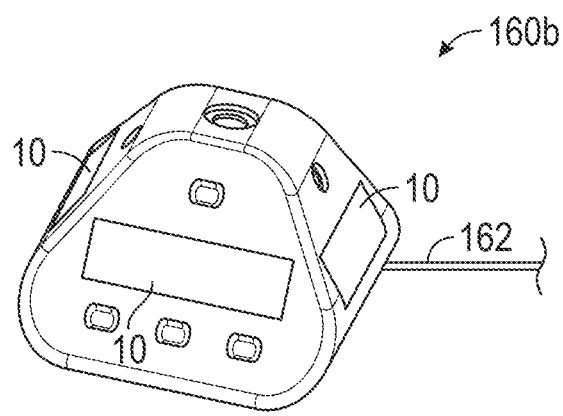
Figure 17D:
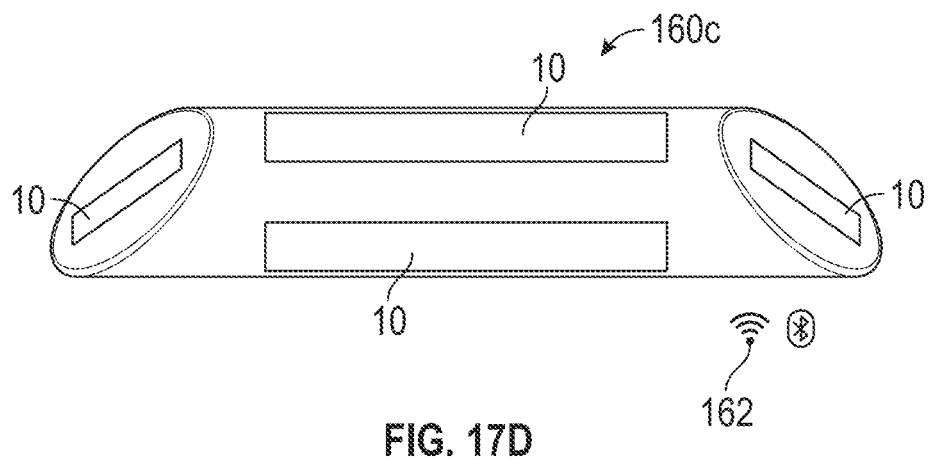

In some embodiments, the medical scanning and mapping systems 10, 10*a*, 10*b*, 10*c*, and/or 10*d*, may be formed as a unitary system 150 as illustrated in FIG. 16. The unitary system 150 may be inserted through the same or a similar sized incision used for a visible light system or robotic surgical manipulators. Generally, the unitary system 150 may include one or more array of camera(s) 18, illuminating fiber(s), and/or optical source(s) 16 within a tubular sleeve 152 that inserts through the same incision used for the visible light system or the robotic surgical manipulators.

The unitary system 150 may allow arrangements of optical source(s) 16 and/or camera(s) 18 suitable for requirements of the triangulation algorithms for meeting the resolution requirements of a given application, without restrictions imposed by the presence of a visible light system. The tubular sleeve 152 may be an elongated cylinder housing the medical scanning and mapping system(s) 10, 10*a*, 10*b*, 10*c*, and/or 10*d*, or any components and configurations thereof. In some embodiments, the tubular sleeve 152 may be a non-circular sleeve maximizing separation between camera(s) 18 and illuminating fiber(s) within the tubular sleeve 152 to increase the depth of tissue for which accurate measurements can be made or permits new configurations of cameras 18 and/or optical sources 16 that provide some measurement advantage but would not fit within a circularly-shaped sleeve. One potential example is an elliptically-shaped sleeve as shown in FIG. 16. Other non-circular and fanciful shapes are contemplated.

Referring to FIGS. 17A-17D, in some embodiments, the medical scanning and mapping system(s) 10, 10*a*, 10*b*, 10*c*, and/or 10*d* may be provided on a platform 160 configured to be positioned within a patient and operated independently of a tubular sleeve. FIGS. 17A-17D depict several exemplary platforms 160, 160*a*, 160*b*, and 160*c* and exemplary networks 162 for connecting to one or more external systems. Generally, the platform 160 may enter through a tubular sleeve inserted into the patient. The platform 160 may be positioned by an operator or surgeon, and then disconnected from the tubular sleeve such that the operator or surgeon is able to use the tubular sleeve for additional instructions and/or tools for the operation and/or procedure. The surgeon or operation may then retrieve the platform 160 and/or remove the platform 160 from the patient using available robotic tools configured to extract the platform 160 through the tubular sleeve. Potential shapes for the platform 160 may include, but are not limited to, pyramids, hemispheres, cones, and slices of spheres that allow for the camera-source pairs, proximity sensors, and visual light systems to scan, measure, and inspect the surrounding tissue through at least, but not limited to, a full hemisphere of solid angle.

The platform 160 may connect to one or more external monitoring and processing systems via the network 162 (e.g., a wired tether, a wireless link) similar to network 13 illustrated in FIG. 1. The network 162 may include, but is not limited to, a Bluetooth connection, or some combination of wired and wireless connections. The network 162 may provide functions that include, but are not limited to, delivery of electronic power, delivery of optical or source power, delivery of control signals, and data telemetry from the platform to the external systems that includes, but is not limited to, signals captured by the proximity sensors and images captured by the infrared and visible light detection systems. The platform 160 can utilize any of the configurations for the medical scanning and mapping systems 10, 10*a*, 10*b*, 10*c*, and/or 10*d* described herein.

Figure 18:
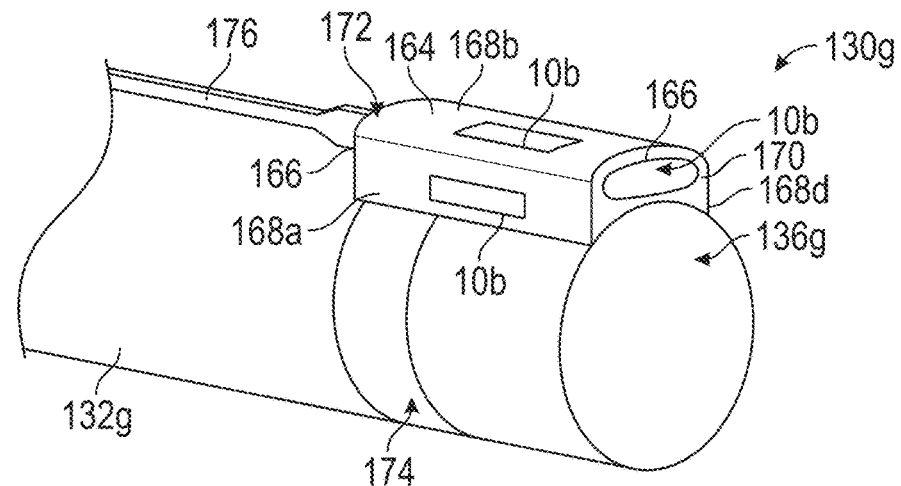
FIG. 18 illustrates one or more medical scanning and mapping systems attached to a separate tubular sleeve or colonoscopy tool in accordance with the present disclosure.

FIG. 18 illustrates one or more medical scanning and mapping systems 10, either individually or in combination, integrated into a separate tubular sleeve 132*g*, colonoscopy tool or other mechanical system suitable for insertion into a patient through incisions, anus or throat, for example. The tubular sleeve 132*g* or other mechanical system may remain independent of the surgical or endoscopic tool used for performing the medical procedure. In some embodiments, the physician or other medical personnel performing the procedure could position the optical scanning hardware component of the one or more medical scanning and mapping systems 10 independently of the surgical or endoscopic instrument. The separate tubular sleeve 132*g* or other mechanical system may utilize any of the arrangements of medical scanning and mapping systems 10 described in embodiments one through eight as hardware of the integrated optical scanning system 130*g*. In some embodiments, the one or more medical scanning and mapping systems 10 may be positioned within a housing 166 having sides 168 positioned between a first end 170 and a second end 172. The one or more medical scanning and mapping systems 10 may be positioned on one or more sides 168, the first end 170 and/or the second end 172. For example, in FIG. 18, medical scanning and mapping systems 10 may be positioned on sides 168*a*, 168*b*, and 168*d*, in addition to having at least one medical scanning and mapping system 10 positioned on end 170. The housing 166 may be positioned about the surgical or endoscopic instrument using an attachment means such as a ring 174 at end 136*g* of the tubular sleeve 132*g* as illustrated in FIG. 18. Other attachment means are contemplated including, but not limited to, adhesive, lock and key, and/or the like. In some embodiments, the medical scanning and mapping systems 10 may communicate via a data cable 176 as illustrated in FIG. 18. However, it should be noted, that communication for the medical scanning and mapping systems 10 may wired or wireless.

Figure 19A:
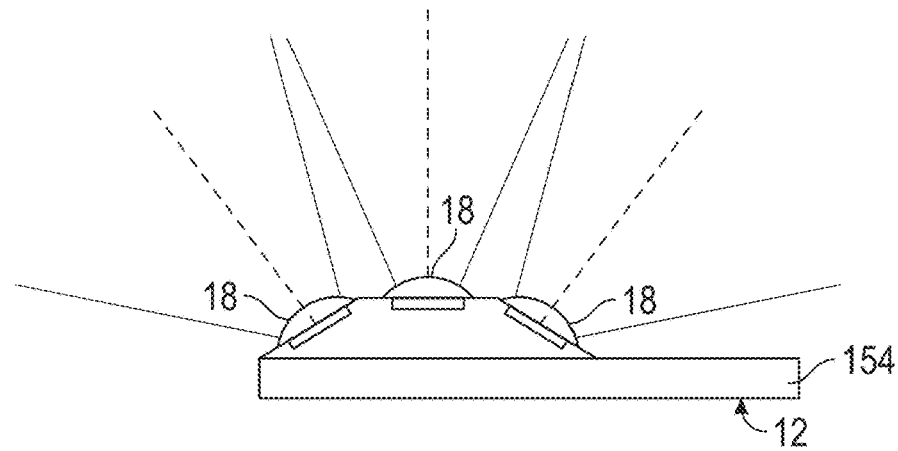
FIGS. 19A and 19B illustrate exemplary mounting methods of multiple cameras for use in medical scanning and mapping systems in accordance with the present disclosure.
Figure 19B:
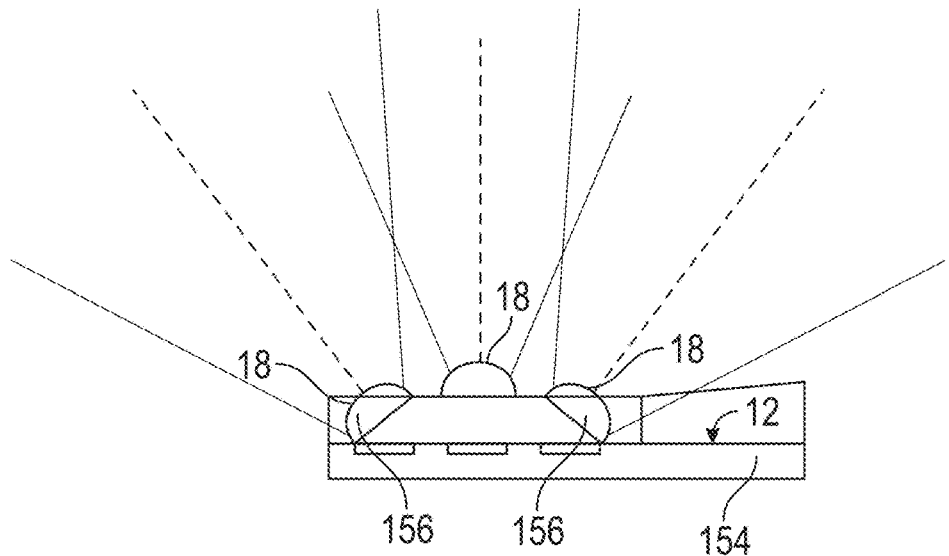

FIGS. 19A and 19B illustrate exemplary mounting methods of multiple cameras 18 for use in the medical scanning and mapping systems 10 described herein. Generally, multiple cameras 18 may be mounted with FOV less than 180° to obtain a total system FOV of greater than or equal to 180° in order to examine and map a larger solid angle in three dimensional space. The FOVs of the individual cameras 18 overlap spatially to ensure that the entire target surface falls within the combined FOV, and that this condition occurs for every distance of interest between the scanning system 10 and the target tissue. The optical source 16 may possess a FOV equal to or greater than the composite FOV of the cameras 18. Methods for combining the FOVs of the individual cameras 18 into a single contiguous FOV include, but are not limited to a different angle with respect to the optical hardware system 12 or the same angle with respect to the optical hardware system 12 as described herein.

FIG. 19A illustrates a method wherein each camera 18 is mounted or positioned at a different angle with respect to a base 154 of the optical hardware system 12, or to the vertical. Tilting the camera 18 shifts the center of the FOV of the camera cone through an angle equal to the tilt angle of the camera 18. Controlling the tilts of each camera 18 in the system 10 may allow the combined cameras 18 to collect light from an extended FOV. For example, in FIG. 19A, three cameras 18 with individual FOV of 60° are co-located with tilts of −60°, 0°, and +60°. The central camera 18 covers the central 60° of the combined FOV, collecting light from angles between −30° and +30°. The side cameras 18 collect light from cones that extend between +30° to +90° and −30° to −90°. The combined cameras 18 collect light from a composite cone extending from −90° to +90° from the vertical, effectively creating a full 180° FOV. Combinations of two, three, or more cameras 18, each camera 18 with an individual FOV of 60° or greater, can generate any number of composite FOVs, even FOVs extending beyond 180°.

Mounting each camera 18 at the same angle with respect to the base 154 of the optical hardware system 12 and adding beam deflecting optics to the light collecting optics may allow each camera to collect light from different but overlapping FOV cones. Beam deflecting optics may include, but are not limited to, optical wedges, prisms, and films or windows with spatially varying refractive index. FIG. 19B shows the operation of such a system utilizing optical wedges 156 to direct light from specific angles onto the recording area of the camera.

Referring to FIG. 1, in some embodiments, the image reconstruction system 14 provides an interactive interface 164 that may allow the surgeon or member of the surgeon's surgical team to interact with the system 14. In one example, the interface 164 may allow a user to select points on the surface model and subsequently provides a measurement of the distance between the points. The interface 164 may include, but is not limited to, a variety of graphics to aid in point selection, visualization of the distance measured, and display of the resulting measurement. The interface 164 may have both touch-screen and standard mouse-keyboard interaction modes to accommodate the computer systems and operating system platforms in use at the operator's site. The interface may incorporate control inputs, which include but are not limited to, controls for adjusting aspects of the system (source power, for example), selection of specific objects or scenes for further analysis, and controls related to overall processing speed such as desired modeling accuracy and acquisition rates.

The image reconstruction system 14 may provide additional tools and/or services to the surgeon or operator to improve the effectiveness of the operator, with the exact tools and services tailored to specific application(s). In one example, the image reconstruction system 14 may contain recognition software to identify and/or locate features of importance to a specific procedure, such as polyps within the colon during a colonoscopy. The interface 164 for this component of the image reconstruction system 14 may include, but is not limited to, sets of icons representing objects or features of interest to a particular procedure that the operator can select, and/or dialog boxes where the operator can enter dimensions or other data related to target objects that act as thresholds beyond which the image reconstruction system 14 may bring objects of interest to the attention of the operator. The recognition software could find smaller polyps or polyps partially obscured by the structure of the colon which a human operator might otherwise miss. The image reconstruction system 14 could provide regular updates of the position of key points identified by the operator—for example, tracking the distance between two edges being sutured to ensure that the edges actually meet instead of having a gap remaining between the edges, or measuring the size of a herniated area to determine the proper sized patch required to repair the hernia.

In an additional embodiment of the image reconstruction system 14, the system may perform provide one or more alarms to indicate when some aspect of the surgical process is incorrect or may cause harm to the patient. In one example, if the medical scanning and mapping system 10 is integrated with a surgical instrument, the image reconstruction system 14 can provide measurement of distances between the surgical instrument and surrounding tissue. The measurement may include forward distance to the tissue, peripheral or side distance to the tissue, or a combination of both measurements, depending on the number and placement of infrared imaging systems around the surgical instrument. The image reconstruction system 14 may also combine the measurements and three dimensional model data collected from the medical scanning and mapping system 10 with visible light images obtained from the visible light components of the imaging system to determine critical information, including but not limited to, the type of tissue the surgical instrument has come in close proximity with (example, the abdominal aorta in laparoscopic surgery). If the distance between the surgical instrument and tissue other than the tissue targeted for the surgery falls below a distance deemed necessary to avoid damage, the image reconstruction system 14 can send an alarm to the user. The alarm may include, but is not limited to, an audio warning, text, or imagery showing the situation that triggered the alarm.

If the medical scanning and mapping system 10 resides on a tubular sleeve separate from the surgical instruments, the image reconstruction system 14 can provide images and measurements that allow the user to determine whether or not the surgical instrument has been inserted correctly and is in danger of damaging tissue other than that which is the target of the surgical procedure. The measurement may include, but is not limited to, the position of the instrument with respect to surrounding tissue and the angle of insertion for the instrument. The image reconstruction system 14 may also combine the measurements and three dimensional model data collected from the optical hardware system 12 with visible light images obtained from the visible light components to determine critical information, including but not limited to, the type of tissue the surgical instrument has come in close proximity with (example, the abdominal aorta in laparoscopic surgery). If the distance between the surgical instrument and tissue other than the tissue targeted for the surgery falls below a distance deemed necessary to avoid damage, or if the angle of insertion is measured to be incorrect, the image reconstruction system 14 can send an alarm to the user. The alarm may include, but is not limited to, an audio warning, text, or imagery showing the situation that triggered the alarm.

In some embodiments, the image reconstruction system 14 may utilize the three-dimensional mapping and measurement data obtained from the images provided by the optical hardware system 12 to synthesize and output control signals useful for operating the surgical or endoscopic systems in a semi-autonomous or fully autonomous manner. In one example, the image reconstruction system 14 may monitor distances between the system 10 and surrounding tissue and the change in the distances as a function of time to determine direction or directions of movement and the speed of movement in one or more directions. The image reconstruction system 14 can predict future positions of the medical scanner and mapping system 10 and/or surgical instruction, and generate signals that control the steering functions of either to achieve specific objectives. Such objectives include, but are not limited to, avoiding contact with surrounding tissue, orienting the medical scanning and mapping system 10 at a specific orientation within the environment, and choosing specific paths through the environment, such as navigating brachial passages in the lungs.

In a semi-autonomous application, action of the image reconstruction system 14 may include, but are not limited to generating control signals to enhance or suppress actions performed by the surgeon or endoscopic operator to meet specific objectives, receiving control inputs from the surgeon or endoscopic operator to change the objectives or focus on specific targets, and receiving signals from the surgeon or endoscopic operator to override the software control signals and assuming full control of the surgical or endoscopic instrument.

In some embodiments, the image reconstruction system 14 can predict future positions of the other instruments and generate signals useful for controlling and/or guiding the operation of the other instruments. In one example, the image reconstruction system 14 may detect the position and orientation of an instrument used to remove a polyp from the colon, including the position and orientation with respect to the polyp targeted for removal. The image reconstruction system 14 may then generate one or more signals capable of moving the instrument to the position and orientation that best ensures complete and precise removal of the polyp, thus minimizing the probability of errors that could allow the remaining components of the polyp to develop into colorectal cancer. The generated signals may completely control the other instruments within the surgical or endoscopic environment or may provide guidance to the operator through the interface components of the software. In another example, the software can detect the position and orientation of a robotic suturing tool and generate control data to cause the suturing tool to precisely position the location of each suture to ensure the suturing meets the strict guidelines set forth by medical professionals to ensure the best possible result for the patient, including the minimization of possible recurrence or future surgeries due to suturing errors.

In some embodiments, the image reconstruction system 14 can analyze the progress of a procedure and determine the timing and extent of procedure documentation. The documentation process may include, but is not limited to, instructing the visible light illumination system, as well as the optical hardware system 12, to collect images of particular features (such as the site of a removed polyp) or end products (such as suturing or installed hernia patch); performing and recording measurements of features deemed important; and documenting any events that have the potential to cause complications for the patient.

The electronics and power systems of the medical scanning and mapping system 10 may provide power, control, data, and processing as needed for the optical source 16 (LED or laser diode), camera 18, and recovery of the image captured by the camera 18.

Driver electronics may provide a constant current drive to the optical source 16, providing an unmodulated optical power output from the optical source 16. Additional electronics may utilize monitoring pins on the optical source 16 or separate monitoring systems to provide control signals used to stabilize the optical power within a desired operating range. The electronics may provide the operator with the means to vary the optical power, either through manual controls (knob, buttons, etc.) or through software interface, so that the user can adapt the instrument for different operating conditions or applications. The electronics can allow the user to switch selected optical sources 16 on or off, allowing the user to select specific sources to use with a selected camera 18. The electronics may also provide clocks and other control signals that may allow the user to control when each optical source 16 turns on, the duration for which the optical source 16 turns on, and the mode (visible or infrared) of the camera 18 capable of recording both visible light and infrared light images.

In some embodiments, a data cable may transmit data collected from camera(s) 18 to the processing electronics and software of the image reconstruction system 14. The cable selected provides sufficient bandwidth to transmit all of the data from the camera 18 quickly, so that the surgeon can respond to measurement results in a timely manner. The cable is shielded to prevent interference between the cable and other electrical instruments and apparatus within the operating theater. Processing and control electronics may allow the user to select which camera(s) 18 the system may use to make measurements and perform initial processing of the camera image. Commercially available hardware may collect data from the camera 18 through the cable and present the data to the image reconstruction system 14 for further processing.

In some embodiments, an inertial measurement unit (IMU) 166 can provide data regarding the movement and orientation of the optical scanning system as surgeon or endoscopic operator moves the physical instrument and the medical scanning and mapping system 10 during the course of a procedure. The IMU 166 may consist of tiny, precision calibrated micro electro-mechanical systems (MEMS) integrated on a chip that measures the angular rate of rotation and linear acceleration in three dimensions. The image reconstruction system 14 may utilize the measurements to track the orientation and position of the medical scanning and mapping system 10 throughout the surgical or endoscopic procedure, providing data critical for steering and pointing the system with high accuracy, either by the human operator or by a semi-autonomous or fully autonomous control system. The measurements may also provide data useful for documenting the procedure for later review and reference From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

The following references are herein incorporated by reference in their entirety:
[1] P. Hauters, J. Desmet, D. Gherardi, S. Dewaele, H. Poilvache, P. Malvoux, "Assessment of predictive factors for recurrence in laparoscopic ventral hernia repair using a bridging technique," Surgical Endoscopy, vol. 31, no. 9, pp. 3656-3663, September 2017.

[2] Dombek M, Lopez C A, Han Z, Lungarini A, Santos N, Schwaitzberg S, Cao C, Jones D B, De S, Olasky J. FUSE certification enhances performance on a virtual computer based simulator for dispersive electrode placement. Surg Endosc. 2018 Feb. 13. PMID: 29442242

[3] Jose L. Porrero, Oscar Cano-Valderrama, Maria J. Castillo, Alberto Marcos, Gabriel Tejerina, Manuel Cendrero, Belen Porrero, Maria T. Alonso, and Antonio J. Torres, "Importance of mesh overlap on hernia recurrence after open umbilical hernia repair with bilayer prosthesis," The American Journal of Surgery, pp. 1-4, 2018.

[4] Gokani S A, Elmqvist K O, El-Koubani O, Ash J, Biswas S K, Rigaudy M, "A cost-utility analysis of small bite sutures versus large bite sutures in the closure of midline laparotomies in the United Kingdom National Health Service," pp. 105-1172018 February 19, doi:10.2147/CEOR.S150176

[5] Deerenberg Eb, Harlaar J J, Steyerberg E W, Lont H E, van Doorn H C, Heisterkamp J, Wijnhoven Bp, Schouten W R, Cense H A, Stockmann H B, Berends F J, Dijkhuizen P H, Dwarkasing R S, Jairam A P, van Ramshorts G H, Kleinrensink G J, Jeekel J, Lange J F, "Small bites versus large bites for closure of abdominal midline incisions (STITCH): a double-blind multicenter, randomized controlled trial,", Lancent. 2015 Sep. 26, pp. 1254-1260. Doi:10.1016/S0140-6736

[6] Henriksen N A, Deerenberg E B, Venclauskas L, Fortelny R H, Miserez M, Muysoms F E, "Meta-analysis on materials and techniques for laparotomy closure: The match review," World J Surg, doi: 10.1007/s00268-017-4393-9. Jan. 10, 2018.

[7] Sri Vengadesh Gopal, Archuthan Warrier, "Recurrence after groin hernia repair-revisited," International Journal of Surgery, ELSEVIER, 11, pp. 374-377, 2013.

[8] ORIGINAL HYPERLINKS REMOVED.

[9] Brittany L. Murphy, Daniel S. Ubl, Jianying Zhang, Elizabeth B. Habermann, David R. Farley, and Keith Paley, "Trends of inguinal hernia repairs performed for recurrence in the United States," Surgery, ELSEVIER, 163, pp. 343-350, 2018.

[10] Carlson M A, Frantzides C T, Shostrom V K, Laguna L E, "Minimally invasive ventral herniorrhaphy: an analysis of 6,266 published cases," Hernia J Hernias Wall Surg, 12 (1), pp. 9-22, 2008.

[11] K, LeBlanc, "Proper mesh overlap is a key determinant in hernia recurrence following laparscopic ventral and incisional hernia repair," Hernia, Springer, doi: 10.1007/s10029-015-1399-9, 2016.

[12] R. S. Decker, A. Shademan, J. D. Opfermann, S. Leonard, P. C. W. Kim, A. Krieger, "Biocompatible Near-Infrared Three-Dimensional Tracking System," IEEE Transactions on Biomedical Engineering, vol. 64, no. 3, March 2017.

[13] Eliza Strickland, "In Flesh-Cutting Task, Autonomous Robot Surgeon Beats Human Surgeons," IEEE Spectrum, Oct. 13, 2017.

[14] Joseph Daniel Bokusky, and Enrique Romo, "Methods and apparatus for constructing endoscopic device with helical lumen design," Auris Surgical Robotics, U.S. Pat. No. 9,844,412, Dec. 19, 2017

[15] Alan Yu, and Jason Lee, "Articulating flexible endoscopic tool with roll capabilities," Auris Surgical Robotics, U.S. Pat. No. 9,561,083, Feb. 7, 2017

[16] Mark Harris, "First Surgical Robot from Secretive Startup Auris Cleared for Use," IEEE Spectrum, Jun. 7, 2016

[17] Alan, Yu, Frederic H. Moll, Benjamin Richter, Mark H. Olson, Jason Gonzalez, Kyle Andrew Tucker, Paxton Maeder-York, and Gregory Schulte, "Surgical robotics system," Auris Surgical Robotics, U.S. Pat. No. 9,622,827, Apr. 18, 2017

[18] David Mintz, Atiyeh Ghoreyshi, Prasanth Jeevan, Yiliang Xu, Gehua Yang, Mathew Joseph Leotta, Charles Stewart, "Navigation of tubular networks," Auris Surgical Robotics, U.S. Pat. No. 9,727,963, Aug. 8, 2017.

[19] Jeffery Alvarez, Jian Zhang and Alisha Seam, "Method, apparatus and a system for robotics assisted surgery," Auris Surgical Robotics, US 2014/0142591, May 22, 2014.

[20] Jason Lee, Christopher Sramek, Gregory Kintz, David Mintz, and Alan Yu, "Floating electromagnetic field generator system and method of controlling the same," Auris Surgical Robotics, US 2017/0290631, Oct. 12, 2017.

[21] Travis Schuh, Mathew Reagan Williams, Joseph Daniel Bogusky, David Mintz, Alan Yu, and Yoichiro Dan, "Instrument device manipulator with back-mounted tool attachment mechanism," Auris Surgical Robotics, US 2017/0367782, Dec. 28, 2017.

[22] Travis Schuh, "Instrument-mounted tension sending mechanism for robotically-driven medical instruments," Auris Surgical Robotics, U.S. Pat. No. 9,788,910, Oct. 17, 2017.

[23] Travis Schuh, "Instrument device manipulator and surgical drape," Auris Surgical Robotics, U.S. Pat. No. 9,737,373, Aug. 22, 2017.

[24] F. Bellocchio, N. A. Borghese, S. Ferrari, V. Piuri, 3D Surface Reconstruction: Multi-Scale Hierarchical Approaches, Chapter 2, Springer, New York, 2013.

[25] G. Frankowski, R. Hainich, "DLP-Based 3D metrology by structured light or projected fringe technology for life sciences and industrial metrology," Proceedings of the SPIE, vol. 7210, pp. 72100C-1 to 72100C-12, 2009.

[26] G. Frankowski, R. Hainich, "DLP/DSP-based optical 3D sensors for the mass market in industrial metrology and life sciences," Proceedings of the SPIE, Photonics West, 2011.

[27] J. Geng, "Structured-light 3D surface imaging: a tutorial," Advances in Optics and Photonics, vol. 3, pp. 128-160, 2011.

[28] K. Harding, ed., "Handbook of Optical Dimensional Metrology," CRC Press, Boca Raton, FL, Chapters 3-5, 2013.

[29] H. Nguyen, D. Nguyen, Z. Wang, H. Kieu, M. Le, "Real-time, high-accuracy 3D imaging and shape measurement," Applied Optics, vol. 54, no. 1, pp. A9-A17, 2015.

[30] T. Yoshizawa, ed., "Handbook of Optical Metrology, 2nd Ed.," CRC Press, Boca Raton, FL, Chapter 15, 2015

[31] Vishnu Vardhan Pully, "Diffuse reflectance spectroscopy for tissues studies and liver vitality check," Politecnico Di Milano, Thesis, 2013.

[32] "Laparoscopic Instruments Market by Product (Laparoscope, Insufflator, Energy Device), Application (Bariatric Surgery, Colorectal Surgery, General Surgery), End User (Hospitals, Ambulatory Surgical Centers)—Analysis & Global Forecast to 2021," MarketsandMarkets.com

[33] "Global Surgical Robotics Market: Focus on Products, Applications, End Users, Countries, Patents, Market Share and Competitive Landscape—Analysis and Forecast (2017-2025)," ResearchAndMarkets.com, posted Jan. 25, 2018.

What is claimed is:

1. A system for providing three-dimensional imaging of a surgical site within a body of a patient during surgery, comprising:
   a medical scanning and mapping system positioned at an end of a tubular sleeve proximate to the surgical site, the medical scanning and mapping system having at least one optical hardware system configured to scan and capture images of a three-dimensional environment within the surgical site, the optical hardware system comprising:
      at least one optical source fixed at the end of the tubular sleeve and configured to illuminate the three-dimensional environment within the body of the patient;
      at least two cameras fixed at the end of the tubular sleeve and configured to capture images of the three-dimensional environment; and
   an image reconstruction system having at least one processor configured to perform image processing, and positioned within the tubular sleeve and configured to process the images to obtain three-dimensional imaging including a depth dimension of the surgical site and provide three dimensional measurements of features within the three-dimensional environment from the three-dimensional imaging of the surgical site; and analyze the three dimensional measurements of the features to provide at least one control signal configured to guide a robotic system within the body.

2. The system of claim 1, wherein the medical scanning and mapping system includes at least one non-transitory processor readable medium, operably coupled to at least one processor, the at least one non-transitory processor readable medium storing processor executable instructions, when executed by the processor, cause the processor to:
   analyze the three dimensional measurements of the features within the three-dimensional environment;
   construct a three dimensional model of the three-dimensional environment; and,
   communicate the control signal configured to guide the robotic system within the body based on the three dimensional measurements of the features and the three dimensional model of the three-dimensional environment.

3. The system of claim 2, wherein the medical scanning and mapping system is configured to analyze the three dimensional measurements of the features to determine location of a target site within the surgical site and the medical scanning and mapping system is configured to analyze the three dimensional measurements to monitor the target site and provide feedback on at least one operation performed by the robotic system.

4. The system of claim 1, wherein the at least two cameras are positioned at different distances relative to the optical source to provide varying levels of resolution along the depth dimension.

5. The system of claim 1, wherein the control signal drives autonomous operation of the robotic system.

6. The system of claim 1, wherein the control signal drives semi-autonomous operation of the robotic system.

7. The system of claim 1, wherein the robotic system is positioned within a colon of the patient.

8. The system of claim 1, wherein the robotic system is positioned within an upper gastrointestinal tract of the patient.

9. A method, comprising:
   inserting a first end of an endoscope into a body of a patient, the first end of the endoscope having an optical hardware system of a medical scanning and mapping system, the optical hardware system having at least one optical source and at least two cameras fixed on the first end of the endoscope;
   positioning the first end of the endoscope at a three-dimensional environment within the body;
   illuminating, using the at least one optical source, the three-dimensional environment within the body;
   capturing, using the at least two cameras, images of the three-dimensional environment; processing the images to obtain three-dimensional imaging including a depth dimension of the three-dimensional environment and obtain three dimensional measurements of features within the three-dimensional environment from the three-dimensional imaging; and,
   analyzing the three dimensional measurements of the features to provide at least one control signal configured to guide the endoscope within the body.

10. The method of claim 9, wherein the optical hardware system is positioned within a colon and configured to provide the at least one control signal to guide and position the endoscope within the colon, with at least one measurement being a real-time measurement.

11. The method of claim 9, wherein the endoscope is positioned at a first location within a colon of the patient and the at least one control signal is configured to autonomously position the endoscope at a second location within the colon.

12. The method of claim 9, wherein the endoscope is positioned at a first location within a colon of the patient and the at least one control signal is configured to semi-autonomously position the endoscope at a second location within the colon such that an operator is capable of overriding the control signal.

13. The method of claim 9, further comprising the step of analyzing the three dimensional imaging and the three dimensional measurements to obtain a set range of movements for the endoscope.

14. The method of claim 9, further comprising the step of analyzing the three dimensional measurements of the features within the three-dimensional environment from the three-dimensional imaging to identify three-dimensional position of a robotic system within the body.

15. The method of claim 14, further comprising the step of analyzing the three dimensional imaging and the three dimensional measurements to locate a target site for sewing of a hernia, by the robotic system, within an abdomen.

16. The method of claim 15, further comprising the step of analyzing the three dimensional imaging and the three dimensional measurements to monitor, by the medical scanning and mapping system, movements of the robotic system during sewing of the hernia.

17. The method of claim 16, further comprising the step of analyzing the three dimensional imaging and the three dimensional measurements to monitor, by the medical scanning and mapping system, the target site for verification sewing of the hernia, by the robotic system, is complete.

18. A method, comprising:
   inserting a first end of an endoscope into a colon of a patient, the first end of the endoscope having an optical hardware system of a medical scanning and mapping system, the optical hardware system having at least one optical source and at least two cameras fixed on the first end of the endoscope;
   positioning the first end of the endoscope at a three-dimensional environment within the colon;
   illuminating, using the at least one optical source, the three-dimensional environment within the colon;

capturing, using the at least two cameras, images of the three-dimensional environment;

processing the images to obtain three-dimensional imaging including a depth dimension of the three-dimensional environment and obtain three dimensional measurements of features within the three-dimensional environment from the three-dimensional imaging; and, analyzing the three dimensional measurements of the features to provide at least one control signal configured to autonomously guide the endoscope within the colon.

19. The method of claim 18, further comprising the step of analyzing the three dimensional measurements of the features within the three-dimensional environment from the three-dimensional imaging to identify a three-dimensional position of a surgical instrument within the colon.

20. The method of claim 18, wherein the endoscope is positioned at a first location within the colon and the at least one control signal is configured to autonomously position the endoscope at a second location within the colon.

\* \* \* \* \*